United States Patent [19]
Gagné et al.

[11] Patent Number: 5,827,927
[45] Date of Patent: *Oct. 27, 1998

[54] MACROMONOMERS HAVING REACTIVE END GROUPS

[75] Inventors: Robert R. Gagné, Pasadena; Matthew Louis Marrocco, III, Santa Ana; Mark Steven Trimmer, Pasadena; Neil H. Hendricks, Brea, all of Calif.

[73] Assignee: Maxdem Incorporated, San Dimas, Calif.

[ * ] Notice: The term of this patent shall not extend beyond the expiration date of Pat. No. 5,824,744.

[21] Appl. No.: 645,914

[22] Filed: May 14, 1996

Related U.S. Application Data

[63] Continuation of Ser. No. 331,144, Oct. 27, 1994, abandoned, which is a continuation of Ser. No. 746,917, Aug. 19, 1991, abandoned.

[51] Int. Cl.$^6$ ..................................................... C08F 8/00
[52] U.S. Cl. ......................... 525/143; 528/128; 528/154; 528/223; 528/225
[58] Field of Search ........................... 525/143; 528/128, 528/154, 223, 225

[56] References Cited

U.S. PATENT DOCUMENTS

| | | | |
|---|---|---|---|
| 3,536,636 | 10/1970 | Tamborski | 528/154 |
| 3,998,864 | 12/1976 | Trevillyan | 260/439 |
| 4,000,187 | 12/1976 | Stille | 260/50 |
| 4,911,801 | 3/1990 | Pons | 204/59 |
| 5,102,971 | 4/1992 | Himmler et al. | 528/167 |
| 5,169,929 | 12/1992 | Tour et al. | 528/397 |

FOREIGN PATENT DOCUMENTS

| | | |
|---|---|---|
| 0436111 | 11/1920 | European Pat. Off. . |
| 0130056 | 1/1985 | European Pat. Off. . |
| 3821567 | 12/1989 | Germany . |
| 1259030 | 10/1989 | Japan . |
| 2113023 | 4/1990 | Japan . |
| 0928576 | 6/1963 | United Kingdom . |
| WO9005754 | 5/1990 | WIPO . |
| WO9102764 | 3/1991 | WIPO . |

OTHER PUBLICATIONS

Rehahn et al., "Soluble poly(para–phenylene)s. 2. Improved synthesis of poly(para–2,5–di–n–hexylphenylene) via Pd–catalysed coupling of 4–bromo–2,5–di–n–hexylbenzeneboronic acid," *Polymer*, 1989, vol. 30, Jun. (1060–1062).
J.M. Tour et al., (1992) Macromol. 25, 499–500.
J. M. Tour et al., (1991) J. Am. Chem. Soc. 113, 2309–2311.
I. Colon et al., (1986) J. Org. Chem. 51, 2627–2637.
M. Rehahn et al., Soluble Poly(para–phenylene(s), 3$^{a)}$), Variation of the Length and the Density of the Solubilizing Side Chains, *Makromol. Chem.* 191, 1991–2003 (1990).
Kallitsis et al, "Synthesis of Some Disubstituted Poly (p–terphenylenes," *Synthetic Metals*, 44 (1991) 247–257.
Wallow et al, Chem. Abs., 115:136902w, 1991.
Wallow et al, "Aqueous Synthesis of Soluble Rigid–Chain Polymers An Ionic Poly(p–phenylene) Analog," Polymer Preprints, American Chemical Society, vol. 32, No. 3, Pub Date Aug. 12, 1991.
Kallitsis et al, Chem. Abs., 96:7293p, 1982.
Liogon'kii et al, Chem. Abs., 96:7293p, 1982.
Matnishyan, A.A., et al, "The Effect of Various Factors on the Synthesis of Polyarylenequinones," Vysokomol. soyed., A13: No. 5, 1009–1017, 1971.
Wallow et al, Chem. Abs., 115:280696z, 1991.
Mezhikovskii et al, Chem. Abs., 78:98152j, 1973.
English–Language version of 78:98152j — Mezhikovskii, S.M. et al "Thermal and Thermo–Oxidative Degradation of Polysulphophenylene–quinones," Vysokomol. soyed., A14: No. 11, 2397–2404, 1972.
Trevillyan, Chem. Abs, 86:139404d, 1977.
Rehahn et al, "Soluble poly(para–phenylene)s. Extension of the Yamamoto synthesis to dibromobenzenes substituted with flexible side chains," Polymer, vol. 30, Jun. 1989, pp. 1054–1059.
Matnishyan et al, "The Effect of Various Factors on the Synthesis of Polyarylenequinones," Vysokomol. soyed., A13: No. 5, 1009–1017, 1971.
Organic Chemistry 3rd Ed. Morrison and Boyd Allyn and Bacon Inc. 1974.

*Primary Examiner*—Yogendra N. Gupta
*Attorney, Agent, or Firm*—Christie, Parker & Hale, LLP

[57] ABSTRACT

A soluble rigid-rod macromonomer is provided which has the following formula:

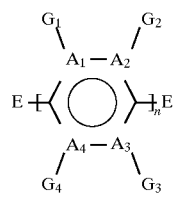

wherein each $A_1$, $A_2$, $A_3$, and $A_4$, on each monomer unit, independently, is C or N, and each $G_1$, $G_2$, $G_3$, and $G_4$, on each monomer unit, independently, is H or a solubilizing side group, provided that at least one monomer unit has at least one solubilizing side group. The solubilizing side groups provide the macromonomers with a solubility of at least 0.5% by weight in the solvent system from which they are formed. E is a reactive end group, and the macromonomer has an average degree of polymerization, $DP_n$, greater than 6. Such macromonomers are chemically incorporated into polymer systems to provide stronger stiffened polymers.

31 Claims, No Drawings

MACROMONOMERS HAVING REACTIVE END GROUPS

This is a continuation of application Ser. No. 08/331,144, filed Oct. 27, 1994, now abandoned; which is a continuation of application Ser. No. 07/746,917, filed Aug. 19, 1991, now abandoned.

FIELD OF THE INVENTION

This invention relates to soluble macromonomers having rigid-rod backbones, pendant, flexible, solubilizing organic groups attached to the backbone, and reactive end groups at the ends of the macromonomer chains. They can be chemically incorporated into other polymer and monomer systems to yield strengthened, stiffened polymer compositions.

BACKGROUND OF THE INVENTION

It is well known that the stiffness and strength of a polymer are related to the flexibility of the polymer chain on the molecular level. Thus, if the chemical structure of the main chain restricts chain coiling and flexing, the resulting polymer will be stiff and strong. An example of a stiff polymer is poly-1,4-pheny-lene-1,4-terephthalamide (PPTA). While PPTA can coil in solution, the amide linkages and para-phenylene groups favor an extended chain conformation. Fibers can be prepared in which the chains are essentially all extended into rod-like conformations, and these fibers are extraordinarily strong and stiff. Unfortunately, PPTA is difficult to process (except for fiber spinning) and cannot be molded or extruded. In general, the more rigid the polymer main chain the more difficult it is to prepare and process.

Some applications require strong, stiff materials that can be easily processed by molding or extrusion. A widely used approach to obtain such stiff materials is to add fillers such as carbon or silica, or to incorporate fibers, such as glass and carbon fibers, into a relatively flexible polymer, thereby forming a stiff, strong composite material. The most widely utilized, high-performance fiber-polymer composites are composed of oriented carbon (graphite) fibers embedded in a suitable polymer matrix.

The improvements in strength and stiffness of composites are related to the aspect ratio of the filler or fiber, i.e., the length to diameter ratio of the smallest diameter cylinder that will enclose the filler or fiber. To contribute reasonable strength and stiffness to the composite, the fibers must have an aspect ratio of at least about 25, and preferably at least 100. Continuous fibers have the highest aspect ratio and yield the best mechanical properties but are costly to process. Low aspect ratio materials, such as chopped fibers and fillers, give limited improvement in mechanical properties but are easy and inexpensive to process. The success of composites is demonstrated by their wide use as structural materials.

There are several drawbacks associated with composite materials. Composites are often more costly than the unreinforced polymer. This is because of the expense of the fiber component and the additional labor needed to prepare the composite. Composites are difficult or impossible to repair and, in general, cannot be recycled. Many composites also have undesirable failure characteristics, failing unpredictably and catastrophically.

Molecular composites (composed of polymeric materials only) offer the prospect of high performance, lower cost and easier processability than conventional fiber-polymer composites. In addition, molecular composites generally can be recycled and repaired. Because molecular composites contain no fibers, they can be fabricated much more easily than fiber-polymer compositions, which contain macroscopic fibers.

Molecular composites are materials composed of a rigid-rod polymer embedded in a flexible polymer matrix. The rigid-rod polymer in a molecular composite can be thought of as the microscopic equivalent of the fiber in a fiber-polymer composite. The flexible polymer component of a molecular composite serves to disperse the rigid-rod polymer, preventing bundling of the rigid-rod molecules. As in conventional fiber/resin composites, the flexible polymer in a molecular composite helps to distribute stress along the rigid-rod molecules via elastic deformation of the flexible polymer. Thus, the second, or matrix-resin, polymer must be sufficiently flexible to effectively surround the rigid-rod molecules while still being able to stretch upon stress. The flexible and rigid-rod polymers can also interact strongly via Van der Waals, hydrogen bonding, or ionic interactions. The advantages of molecular composites have been demonstrated by W. F. Hwang, D. R. Wiff, C. L. Brenner and T. E. Helminiak, *Journal of Macromolecular Science Phys,* B22, 231–257 (1983).

Molecular composites are simple mixtures or blends of a rigid-rod polymer with a flexible polymer. As is known in the art, most polymers do not mix with other polymers, and attempts at blends lead to macroscopic phase separation. This is also true of rigid-rod polymer/flexible polymer blends. Metastable blends may be prepared by rapid coagulation from solution. However, metastable blends will phase separate on heating, ruling out further thermal processing, such as molding or melt spinning. The problem of macroscopic phase separation is reported by H. H. Chuah, T. Kyu and T. E. Helminiak, *Polymer,* 28, 2130–2133 (1987). Macroscopic phase separation is a major limitation of molecular composites.

Rigid-rod polymers produced in the past are, in general, highly insoluble (except in the special case of polymers with basic groups, which may be dissolved in strong acids or in organic solvents with the aid of Lewis acids) and infusible. Preparation and processing of such polymers is, accordingly, difficult. A notable exception is found in U.S. Pat. application Ser. No. 07/397,732, filed Aug. 23, 1989 now U.S. Pat. No. 5,227,457 (assigned to the assignee of the present invention), which is incorporated herein by this reference. The rigid-rod polymers described in the above-referenced application have a rigid-rod backbone comprising a chain length of at least 25 organic monomer units joined together by covalent bonds wherein at least about 95% of the bonds are substantially parallel; and solubilizing organic groups attached to at least 1% of the monomer units. The polymers are prepared in a solvent system that is a solvent for both the monomer starting materials and the rigid-rod polymer product. The preferred monomer units include: paraphenyl, parabiphenyl, paraterphenyl, 2,6-quinoline, 2,6-quinazoline, paraphenylene-2-benzobisthiazole, paraphenylene-2-benzobisoxazole, paraphenylene-2-benzobisimidazole, paraphenylene-1-pyromellitimide, 2,6-naphthylene, 1,4-naphthylene, 1,5-naphthylene, 1,4-anthracenyl, 1,10-anthracenyl, 1,5-anthracenyl, 2,6-anthracenyl, 9,10-anthracenyl, and 2,5-pyridinyl.

The rigid-rod polymers described above can be used as self-reinforced engineering plastics and exhibit physical properties and cost-effectiveness superior to that exhibited by many conventional fiber-containing composites.

It would be quite useful if rigid-rod polymers could be incorporated into conventional flexible polymers, especially large volume commodity polymers. The value of a flexible polymer would be increased significantly if its mechanical properties could be enhanced by addition of rigid-rod polymers. Such molecular composites could displace more expensive engineering resins and specialty polymers and conventional composites as well. To date, practical molecular composites have not been demonstrated. This is chiefly due to deficiencies in currently available rigid-rod polymers, namely limited solubility and fusibility, and unfavorable chemical and physical interactions between the rigid-rod and flexible polymer component.

There is a need in the art for a rigid-rod polymer that can be chemically incorporated into flexible polymers and polymer systems, during or subsequent to polymerization, to thereby add strength and/or stiffness to the resulting polymers. Chemical rather than physical incorporation is desirable to inhibit phase separation during the processing and use of the polymer and to increase the resulting polymer's solvent resistance. The mechanical behavior of polymer systems which contain chemically incorporated rigid-rod moieties can be different and superior to physical blends of, for example, rigid-rod polymers with flexible polymers.

SUMMARY OF THE INVENTION

It has now been found that, for any given polymer, improvements in stiffness and strength can be obtained by preparing a copolymer, thermoset resin, or the like, which incorporates rigid segments and the more flexible segments of the original polymer. These rigid segments act in a manner conceptually similar to the way stiff fibers act to reinforce composites; however, in the present invention no macroscopic fibers are present.

In the present invention, the problem of macroscopic phase separation, found in molecular composites, is avoided by the use of rigid-rod macromonomers having reactive end groups. In one embodiment of the present invention, the rigid-rod macromonomers are made to react with flexible polymers, via reactive end groups, to form covalent bonds between the rigid-rod macromonomer and the flexible polymer, thereby preventing macroscopic phase separation.

In a second embodiment, macroscopic phase separation is prevented by forming the flexible polymer in the presence of the macromonomer. The reactive end groups of the macromonomer react with monomers during polymerization of the flexible polymer, forming covalent bonds between the macromonomer and flexible polymer.

In a third embodiment, the rigid-rod macromonomer is modified, by way of chemical transformation of its reactive end groups, such that the end groups are made compatible with the flexible polymers. Compatibilizers include groups which will interact with the flexible polymer ionically, by hydrogen bonding, or by van der Waals interactions. Compatibilizers may be polymeric, or oligomeric. For example, a rigid-rod macromonomer may be made to react, via its reactive end groups, with caprolactam to form short polycaprolactam chains at either end, the resulting polycaprolactam-modified macromonomer being compatible with polycaprolactam.

In a fourth embodiment, the rigid-rod monomers are used alone to form thermosetting resins. In this case, the reactive end groups provide some degree of processability and will react under the appropriate conditions, e.g., heat, irradiation, exposure to air, etc., to form crosslinks and effect curing.

Other methods of incorporating the rigid-rod macromonomers of the present invention into materials are contemplated and depend on the chemistry and properties of the material to be modified.

It should be understood that while macroscopic phase separation is prevented, there may be varying degrees of microscopic phase separation. Microscopic phase separation results in the formation of phases having size on the order of the dimensions of the polymer chain. Microphase separation may be conducive to significant improvements in mechanical or other properties desired from incorporation of rigid-rod macromonomers.

The macromonomers of the present invention have the structure (1):

where each $G_1$, $G_2$, $G_3$, and $G_4$, on each monomer unit, independently, is a solubilizing side group or hydrogen, E is a functional ("reactive") end group, and the number average degree of polymerization, $DP_n$, is greater than about 6. If $DP_n$ is less than about 7 or 8, the rigidity and stiffness of the resulting macromonomer-reinforced polymer is only slightly increased. In some applications, however, macromonomers prepared in accordance with the present invention having a $DP_n$ as low as 4 may be useful, e.g., for decreasing the thermal expansion coefficient of a flexible polymer, such as a polyimide or polyamide. Preferably, $DP_n$ is between 10 and 500. G will be used to mean a general solubilizing group and $G_1$, $G_2$, $G_3$, and $G_4$ specific solubilizing groups.

The structures presented here show only a single monomer unit and do not imply regular head-to-tail arrangement of monomer units along the chain. Monomer units may have random orientation, or may be alternating head-to-head, tail-to-tail, or regular head-to-tail, or have other arrangements, depending on the conditions of the polymerization and reactivity of monomers.

The macromonomers of the present invention may also contain heteroatoms in the main chain. Heteroaromatic rigid-rod macromonomers have structure (2), where $A_1$, $A_2$, $A_3$, and $A_4$ on each monomer unit, independently, may be carbon or nitrogen and G and E are as defined above, except that where an A is nitrogen, the corresponding G is nil.

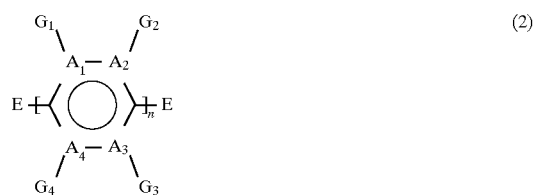

Additionally, other rigid-rod monomer units can be incorporated into the macromonomers prepared in accordance with the present invention. Thus a rigid-rod macromonomer having monomer units of the type shown in structures (1) and/or (2) and benzobisthiazole monomer units

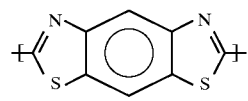

can be used in the same way as (1) and (2). Likewise, rigid-rod pyromellitimide, benzobisoxazole, benzobisimidazole and other rigid-rod monomer units may be substituted for some of the phenylene units without loss of function. The benzobisimidazole, thiazole and oxazole units can have either cis or trans configuration.

The rigid-rod macromonomers of the present invention may be further polymerized or cured by virtue of their reactive end groups. Depending on the nature of the end groups and cure conditions, either linear, branched or network structures result.

The macromonomers of the present invention may be used to form thermosets, either alone or in combination with other thermosetting polymers. The macromonomers may also be used with thermoplastics, e.g., by forming a copolymer.

DETAILED DESCRIPTION OF THE INVENTION

As discussed above, the strength and stiffness of a polymer are related to the flexibility of the polymer chain on a molecular level. It has now been found that for any given polymer, improvements in stiffness and strength can be obtained by preparing a copolymer having rigid segments as well as the more flexible segments of the original polymer. These rigid segments act in a manner conceptually similar to the way stiff fibers act to reinforce composites, however, in the present invention no macroscopic fibers are present. The rigid segments are provided by incorporating rigid-rod macromonomers having structures (1) and/or (2) during or subsequent to polymerization of the flexible polymer. Several approaches are provided by the present invention.

Macromonomers having structure (1) are solubilized polyparaphenylenes having reactive functional end groups. Macromonomers having structure (2) are aza derivatives of polyparaphenylenes having reactive end groups. In each case, $G_1$ through $G_4$ are solubilizing side groups or hydrogen, E is a functional end group, and the number average degree of polymerization, $DP_n$ is greater than about 6, preferably between 10 and 500.

As used herein, the term "endcapper" shall mean any reagent which serves to terminate growth of one or both ends of the macromonomer being formed, thus preventing further extension of the rigid-rod macromonomer backbone via the ongoing macromonomer-forming reaction, and which results in a "reactive end group", E, being chemically incorporated into that end of the rigid-rod macromonomer molecule.

The terms "reactive end group," "functional end group," and the like, are defined to mean any chemical moiety incorporated into an end of a rigid-rod macromonomer molecule, which chemical moiety can be used in a subsequent reaction to effect one or more of the following reactions:

a) Reaction with a flexible polymer resulting in formation of one or more covalent bonds between the macromonomer and the flexible polymer;

b) Reaction with monomers, either before or during a reaction in which such monomers are polymerized to give a flexible polymer, resulting in formation of one or more covalent bonds between the macromonomer and the resulting flexible polymer;

c) Reaction with an oligomer or other small molecular species, resulting in increased compatibility of the rigid-rod macromonomer with flexible polymers in blends, mixtures, composites, copolymers, composites, alloys and the like; and d) Polar, ionic, or covalent interaction with an inorganic matrix, resulting in a modified ceramic or an inorganic glass or glass-like material.

Reactive groups may be transformed by further chemical reaction including, without limitation, oxidation, reduction, deprotonation, halogenation, Schiff base formation, hydrolysis, electrophilic or nucleophilic substitution, and the like, to yield new reactive groups.

One skilled in the art will recognize that it sometimes will be desirable to incorporate such endcapper reactive groups in a protected form in order to ensure that the reactive group does not poison or otherwise participate in or interfere with the macromonomer-forming reaction, e.g., an amine can be incorporated as an amide, a carboxylic acid can be incorporated as an ester, and an alcohol can be incorporated as an ester or as an ether. Once formation of the macromonomer has been completed the protected reactive end group can then be deprotected, e.g., an amide or an ester can be hydrolyzed to produce an amine and an alcohol, respectively.

Nonlimiting examples of reactive end groups, E, include acetals, acetals from ethylvinylether, acetylenes, acetyls, acid anhydrides, acids, acrylamides, acrylates, alcohols, aldehydes, alkanols, alkyl aldehydes, alkyl halides, amides, amines, anilines, aryl aldehydes, azides, benzocyclobutenes, biphenylenes, carboxylates, carboxylic acids and their salts, carboxylic acid halides, carboxylic anhydrides, cyanates, cyanides, epoxides, esters, ethers, formyls, fulvenes, halides, heteroaryls, hydrazines, hydroxylamines, imides, imines, isocyanates, ketals, ketoalkyls, ketoaryls, ketones, maleimides, nitriles olefins, phenols, phosphates, phosphonates, quaternary amines, silanes, silicates, silicones, silyl ethers, styrenes, sulfonamides, sulfones, sulfonic acids and their salts, sulfonyl halides, sulfoxides, tetrahydropyranyl ethers, thioethers, urethanes, vinyl ethers, vinyls, and the like. In some cases, the functional end groups are capable of reacting with each other.

One skilled in the art will recognize that reactive groups can be prepared from "non-reactive" groups and "less reactive" groups. For example, some applications make it desirable to incorporate a rigid rod polymer having tolyl end groups into a flexible polyester. The tolyl group is unreactive toward polyesters or polyester monomers, however, the tolyl group can be oxidized to a reactive carboxyphenyl group which then can react with polyesters by trans-esterification, or with polyester monomers to form polyesters containing the rigid rod macromonomer. Similarly, a relatively non-reactive acetyl group can be modified by formation of a Schiff's base with 4-aminophenol, to give a macromonomer having phenolic end groups, useful for reinforcing thermoset resins such as epoxies and phenolics. Other examples will be apparent to those skilled in the art.

The term "solubilizing side group" as used herein means a chemical moiety which, when attached to the backbone of the macromonomer, improves the solubility of the macromonomer in an appropriate solvent system. For the purposes of the present invention, the term "soluble" will mean that a solution can be prepared containing greater than 0.5% by weight of the macromonomer or greater than about 0.5% of the monomer(s) being used to form the macromonomer.

It is understood that various factors must be considered in choosing a solubilizing group for a particular polymer and solvent, and that, all else being the same, a larger or higher molecular weight solubilizing group will induce a higher degree of solubility. Conversely, for smaller solubilizing groups, matching the properties of the solvent and solubilizing groups is more critical, and it may be necessary to have, in addition, other favorable interactions inherent in the structure of the polymer to aid in solubilization.

In some embodiments of the invention, some of the side groups G will also be "reactive" functional groups, in the same sense that the end groups E are reactive.

The number average degree of polymerization, $DP_n$ is defined by:

$DP_n$=(number of monomer molecules present initially)/(number of polymer or oligomer chains in the system).

The number average molecular weight, $M_n$ is defined by:

$$M_n = M_o \times DP_n$$

where $M_o$ is the weight of one monomer unit in the chain. We will use a convention where the end groups are not counted in figuring the $DP_n$. The end groups make only small contribution to the molecular weight and are not included in the definition.

As described below in greater detail, the rigid-rod macromonomers of the present invention are formed by reacting a macromonomer with an "endcapper" or endcapping moiety. The endcapper provides the functional end group E, directly or by chemical transformation (including, e.g., deprotection) into E.

For an ideal condensation polymerization, $DP_n$ may be calculated given the initial amounts of monomer and endcapper described below by:

$$DP_n = 2 \times \text{mols monomer/mols endcapper.}$$

In practice, this is usually an upper limit due to adventitious endcapping reactions which lower the molecular weight of the macromonomer. When adventitious endcappers (impurities) are present, $DP_n$=2×mols monomer ÷[(mols of endcapper)+(mols of adventitious endcapping impurities)]. If the amount of adventitious endcapper is small, then the observed $DP_n$ will be close to that which is calculated neglecting impurities.

Side reactions will also limit molecular weight of the macromonomers. Side reactions may be accounted for in calculation of $DP_n$ by including a term for the extent of reaction, as described below in the discussion following General Procedures I–III.

The number average degree of polymerization $DP_n$ is indicated in structural formulae, as in structure (1), by "n".

Compounds having structure (1) or (2) are rigid-rod macromonomers having reactive end groups. Such macromonomers are rigid or stiff on both the microscopic and macroscopic level. These macromonomers can be incorporated into other polymers via the two reactive end groups, E, and will impart stiffness and strength to the resultant polymers. Compounds of this type are sometimes called telechelic polymers or telechelic oligomers. The distinction between oligomers and polymers is that the properties of an oligomer change measurably on changing the degree of polymerization by one, while for a polymer adding an additional monomer unit has little effect on properties. Since the range of $DP_n$ (>6) considered here covers both oligomers and polymers, and since this technical distinction is not of great importance to the applications of these compounds, we will use the term macromonomer to imply the entire range from oligomers to polymers.

In macromonomers having structure (2), if only one of the A's is nitrogen, for example if $A_4$ is N, substituted polypyridines of structure (3) result:

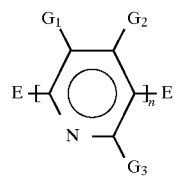

(3)

If only $A_1$ and $A_2$ are N, the monomer unit is a pyridazine; if only $A_1$ and $A_3$ are N, the monomer unit is a pyrazine, if only $A_1$ and $A_4$ are N, the monomer unit is a pyrimidine. If three A's are N, the monomer unit is a triazine. Other heterocyclic monomer units are included if some of the G's are bridging, for example, if $G_1$ and $G_2$ are —CHCHCHCH—, and $A_3$ is N, the monomer unit is an isoquinoline.

Macromonomers having the structure (2) include compounds of the structure (1) as a subset.

It is possible to have rigid-rod macromonomers in accordance with the present invention comprising several types of monomer units, each with a different set of A's and G's, i.e., each $A_1$, $A_2$, $A_3$ and $A_4$ on each monomer unit, independently is C or N, and each $G_1$, $G_2$, $G_3$, and $G_4$ on each monomer unit, independently is H or a solubilizing side group. In other words, adjacent monomer units need not be identical. Macromonomers comprised of different monomers are copolymer-type macromonomers and are usually prepared using more than one monomer.

As stated above, the number and type of side groups necessary to impart solubility will depend on the solvent, n and the nature of E. If n is small, only a few side chains will be needed for solubility. That is, only some of the monomer units in each chain may be substituted; the rest are unsubstituted, i.e., the G's are all H. Where n is very small and E aids solubility, all the G's may be H. Where n is large, solubility may be maintained by using more non-H G's per chain or by using G's with higher molecular weight. In many cases, the macromonomer will have exactly one non-hydrogen G per monomer unit, i.e. $G_1$=solubilizing group, $G_2$=$G_3$=$G_4$=H. Structures (1) and (2) are meant to imply both homopolymers and copolymers where not all monomer units have the same set of G's.

The macromonomers of the present invention may interact differently with different classes of flexible polymers, for example, addition polymers and condensation polymers. A nonlimiting list of flexible polymers that can incorporate the macromonomers of the present invention includes polyacetals, polyamides, polyimides, polyesters, polycarbonates, polyamide-imides, polyamide-esters, polyamide ethers, polycarbonate-esters, polyamide-ethers, polyacrylates; elastomers such as polybutadiene, copolymers of butadiene with one or more other monomers, butadiene-acrylonitrile rubber, styrene-butadiene rubber, polyisoprene, copolymers of isoprene with one or more other monomers, polyphosphazenes, natural rubber, blends of natural and synthetic rubber, polydimethylsiloxane, copolymers containing the diphenylsiloxane unit; polyalkylmethacrylates, polyethylene, polypropylene, polystyrene, polyvinylacetate; polyvinylalcohol, and polyvinylchloride.

Reinforcing Condensation Polymers

Rigid segments may be introduced into a wide variety of condensation polymers through the use of the rigid-rod macromonomers of the present invention. In one embodiment, the macromonomer is added during the polymer forming reacting (polymerization) of the polymer to be stiffened. The polymer to be stiffened and/or strengthened will be referred to as the flexible polymer, regardless of its absolute stiffness. In one embodiment, in addition to being rigid, the macromonomer will dissolve in the flexible polymer polymerization dope and have functionality enabling it to take part in the polymerization reaction. In another embodiment, the initially formed flexible condensation polymer is isolated, and a solvent is selected for both the macromonomer and the flexible polymer. The flexible polymer and macromonomer are redissolved, and the macromonomer reacts with the originally formed flexible polymer. Macromonomers may also be dissolved in the melt of the flexible polymer, where reaction of the end groups may then occur.

Several types of condensation polymers may be distinguished. Condensation polymers may include a single monomer, usually referred to as an A-B monomer:

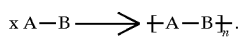

Alternatively, two complementary difunctional monomers, usually referred to as A—A and B—B may be condensed:

Where the rigid-rod macromonomers are used in a condensation polymerization, they may be considered A—A (or B—B) type monomers. That is, the two reactive end groups E can be considered to be the A—A (or B—B) type end groups typically described in condensation polymerization systems. A—A, B—B, and A—B type monomers are described in U.S. Pat. No. 4,000,187 to Stille, incorporated herein by this reference. For purposes of the present invention, the designation of particular monomers as being "A—A" or "B—B" is arbitrary, so long as A and B are complementary functionalities. Thus A—A can represent a diamine, e.g., and B—B a diacid, and vice versa. If more than one type of macromonomer is used they may be conveniently distinguished by denoting them by "AMA", "A'MA'", "BMB", "B'MB'", and so forth.

Nonlimiting examples of A—A and B—B type monomers include diamine-type monomers such as p-phenylenediamine, m-phenylenediamine, oxydianiline, methylenedianiline, tetramethylenediamine, hexamethylenediamine; diol-type monomers such as resorcinol and hexanediol; bisaminoketones, bisthiols; diacid-type monomers such as adipic acid, adipoyl chloride, esters of adipic acid, terephthalic acid, terephthaloyl chloride, esters of terephthalic acid; bisketomethylenes, bis(activated halides) such as chlorophenyl sulfone, and the like.

Nonlimiting examples of A—B type monomers include amino acids, amino acid esters, activated halides such as 4-fluoro-4'-hydroxybenzophenone, lactams (e.g., caprolactam), lactones, and the like.

Several types of reinforced polymers and copolymers are possible with rigid macromonomers. Let AMA (or BMB) represent a rigid macromonomer. In the simplest case AMA is condensed with a B—B monomer:

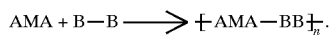

The resulting copolymer will incorporate rigid AMA macromonomer blocks separated by single B—B type monomer units.

A copolymer also can be formed using AMA macromonomers in conjunction with a second A—A monomer having similar end functionality, and a B—B monomer:

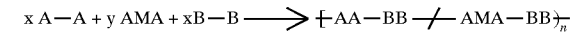

where the symbol "/" indicates a random copolymer. The relative amount of rigid segments is determined by the ratio of x to y, that is by the ratio of A—A monomer to AMA macromonomer used. As is known in the art, the degree of polymerization, indicated by n, may be controlled by controlling the monomer balance, that is the ratio of B—B monomer to the total of A—A and AMA monomers, where x+y=z is perfect balance and gives highest n.

Rigid macromonomers AMA when used with A—B monomers result in tri-block copolymers when the molar amount of A—B monomer is large relative to AMA:

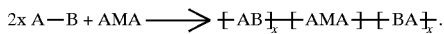

In general the macromonomer will form the center block with AB blocks at the ends. If A—B is not in molar excess, mixtures of di and tri blocks, e.g., may result.

More complex mixtures of rigid macromonomers with A—A, B—B and A—B monomers are also possible. Order of addition and control of monomer imbalance can be used to create complex block copolymers. Any set of A—A, B—B and A—B monomers which will co-condense with an AMA (or BMB) type macromonomer will be called complementary monomers. For example, terephthalic acid and ethylene glycol are complementary monomers that will condense with the AMA-type macromonomers of the present invention. Similarly, a co-polyester can be formed by condensing AMA-type macromonomers having structure (1) or (2) with one or more complementary monomers such as biscarboxylic acids, biscarboxylic acid halides, biscarboxylic acid esters, bisdiols, hydroxycarboxylic acids, lactones, and the like.

Two variables which may be used to control the properties of the copolymers having macromonomers incorporated therein are: the average length of the rigid segments, $L_r$, which is proportional to $DP_n$, and the weight fraction of rigid segments in the copolymer, $W_r$.

If A—B and/or A—A type monomers are present along with AMA and B—B type monomers, $W_r$ is lowered. The molecular weight ratio can also be changed by changing the macromonomer M.

Reinforcing Thermoset Resins

The rigid-rod macromonomers of the present invention may also be used to form thermoset resins, either alone or in conjunction with existing thermoset formulas to impart strength, stiffness, and/or a lower coefficient of thermal expansion. Thermosets are often formed in stages, where monomers are allowed to react to a limited extent to give a processable resin, which is cured in a second stage, often by heat treatment. Thermosets are typically crosslinked, and the stages are defined by the degree of crosslinking. Aside from the insoluble, infusible nature of the resulting cured thermoset, the chemistry is similar to condensation polymers. Diols, polyols, diamines and polyamines are commonly used thermoset precursors that will react with the macromonomers of the present invention.

Rigid-rod polymers heretofore have not been used in thermosets, primarily because it is commonly thought that rigid-rod polymers are not soluble in resin systems, including solutions of resins or pre-polymers used to prepare thermoset resins. The rigid-rod macromonomers of this invention, however, are soluble in common solvents, and can be made compatible with various resin systems by proper choice of side groups, G. The end groups E also should be compatible with the cure chemistry of the thermoset.

Typically, but not necessarily, E will be chosen to match the reactive groups in the thermoset. For example, E should be an epoxy group or an amino group for use with an epoxy resin, or a phenol group for use with phenolic resins. It is also usually desirable for the cure temperatures of the end groups E and the thermoset to be similar. Nonlimiting examples of thermoset systems which can incorporate the rigid-rod macromonomers of the present invention are: allyl resins, benzophenonetetracarboxylic acid or its anhydride, bisacetylene resins, bisbenzocyclobutene resins,, bisbiphenylene resins, bisphenoltetracarboxylic acid or its anhydride, diepoxides, epoxy resins, formaldehyde and paraformaldehyde-based resins, furan resins, phenolic resins, polyepoxides, pyromellitic acid or its anhydride, trioxanes, phenol-formaldehyde resins, nrovolac resins, resole resins, resorcinol-formaldehyde resins, silicone resins, urethanes, melamine resins, isocyanate resins, resins based on cyanuric acid and cyanuric chloride, polyamic acids, polyamide resins, crosslinked polyamides and polyesters, unsaturated polyester resins, urea resins, vinyl ester resins, and natural resins, gums, lacquers and varnishes.

The rigid-rod macromonomers of the present invention may also be used alone to form thermosetting resins. In this case, the side groups G are not needed for solubility in,, or compatibility with, other resins, polymers or monomers, but impart some degree of thermoformability. In general, rigid-rod macromonomers with smaller n will have lower glass transition temperatures and melting temperatures, and will be more readily heat processed. As is known in the art it is necessary to adjust the melting temperature and cure temperature so that the polymer system does not cure before it is thermoformed, and so that unreasonably high temperatures are not needed for curing.

When used as a thermoset, the rigid-rod macromonomer must have sufficient flow properties to be shaped or processed, typically at elevated temperatures. Thus, the side groups G and the $DP_n$ are chosen to allow some degree of thermoformability. In general, larger and more flexible G's increase processability, as does lower $DP_n$. On the other hand, smaller G's and larger $DP_n$'s enhance stiffness and strength, so that optimum sizes for $DP_n$ and G can be found. Different processing methods will have different requirements; for example, sintering does not require complete melting, whereas injection molding requires low viscosity melts. The reactive end groups E of a rigid-rod macromonomer for use as a thermoset should have a cure temperature consistent with the required processing temperature. If the cure temperature is too low, the material will cure before processing can be completed. If the cure temperature is too high, the material may not fully cure or the flow properties at the curing temperature may be undesirable. In an exemplary and nonlimiting embodiment of the invention, cure is effected by using a curing agent such as a catalyst or low molecular weight crosslinking agent.

Non-limiting examples of reactive end groups with good cure temperatures are maleimides, nadimides, and acetylenes.

Reinforcing Addition Polymers

The rigid-rod macromonomers of the present invention also find use as pre- and post-polymerization additives. As post-polymerization additives, rigid-rod macromonomers may be used in compounding, blending, alloying, or otherwise mixing with preformed polymers, preformed blends, alloys, or mixtures of polymers. In these cases the side groups and end groups help make the macromonomer compatible with the polymer to be reinforced. Such compounding, blending, alloying etc. may be done by solution methods, melt processing, milling, calendaring, grinding or other physical or mechanical methods, or by a combination of such methods. Chemical reaction of the end groups E of the macromonomer with the polymer into which the macromonomer is being incorporated may take place during such processes or E may simply make the rigid segment M compatible with the proformed polymer, for example via non-covalent interactions, including hydrogen bonding, ionic bonding and van der Waals forces. Mechanical heating or shearing can initiate such chemical processes which will effect the final composition.

For many addition polymers, where it is not convenient to introduce the macromonomer during polymerization, the rigid-rod macromonomer may be introduced by the above methods in post-polymerization processes. Nonlimiting examples of such polymers include, polyethylene, polypropylene, polyvinylchloride, polystyrene, polyacrylonitrile, polyacrylates, ABS, SBR, and other homopolymers, copolymers, blends, alloys etc. The above methods may also be used with condensation polymers.

As pre-polymerization additives, the macromonomers of the present invention are added along with other monomers to be polymerized to yield the final polymer.

Optionally, conventional fillers such as carbon black, silica, talc, powders, chopped or continuous fibers, or other macroscopic reinforcing agents as are known in the art can be added to the polymer systems which incorporate the rigid-rod macromonomers of the present invention. In embodiments of the invention in which macroscopic reinforcing agents are added, the macromonomers of the present invention add additional strength, stiffness, creep resistance, fire resistance, toughness and/or other properties to what would otherwise be conventional composites and resins and also serve to decrease the amount of filler used in a conventional composite or resin.

The rigid-rod macromonomers of the present invention may be used to enhance the properties of all types of natural and synthetic polymers, including but not limited to, addition polymers, condensation polymers, ring opening polymers, thermosets, thermoplastics, elastomers, rubbers, silicones, silicone rubbers, latexes, gums, varnishes, and cellulose derived polymers.

When used with rubbers and elastomers having a polymer network the rigid rod macromonomers act to modify such properties as strength, abrasion resistance, resilience, wear resistance, creep, and the like, and may be used to replace or eliminate the use of fillers.

The reinforced polymers of the present invention may be used to fabricate films, fibers, and molded parts having improved properties, especially improved mechanical properties, relative to the same material without reinforcement by rigid-rod macromonomers. Other non-limiting examples of applications of the reinforced polymers of the present invention include adhesives, elastomers, coatings, membranes, plastic sheet, and sheet molding compounds.

Preparation of Macromonomers Having Functional End Groups

In order to introduce rigid segments into a wide variety of polymers a rigid-rod type macromonomer is first prepared. The poly-1,4-phenylene structure (1) and aza derivatives (structure (2)) offer a stiff, strong, thermally stable, and chemically inert backbone, of potentially low cost.

Several methods may be used to prepare poly-para-phenylenes and aza analogs. The simplest rely on reductive condensation of 1,4-dihaloaromatics, either by way of a Grignard reagent, or directly in the presence of a reducing agent such as zinc metal. A catalyst, such as bis (triphenylphosphine) nickel (II) chloride or 1,4-dichloro-2-butene is used. Para-bromoaryl boronic acids may be coupled using palladium based catalysts. Polyphenylenes have also been prepared by methods which do not give exclusive para linkage, such as Diels-Alder condensation of bis-acetylenes and bis-pyrones, polymerization of 1,3-cyclohexadiene followed by aromatization and oxidative polymerization of benzene.

The rigid-rod macromonomers of the present invention may be made by these and other methods, keeping in mind the special requirements of side groups and end groups. The catalytic reductive coupling of 1,4-dihaloaryls is preferred, (and more preferably, reductive coupling of 1,4-dichloroaryls) because of its simplicity and wider tolerance of functional groups. The special nature of the rigid-rod macromonomers of the present invention must be taken into account in order to successfully prepare these macromonomers.

The synthesis of even short rigid-rod molecules is made difficult by their low solubility. For example, poly-1,4-phenylene (structure (1), where $G_1$ through $G_4$ and E are each hydrogen) compounds with n greater than about 8 are essentially insoluble in all solvents, and are infusible. Solubility is achieved in the present invention by appropriate choice of solubilizing groups G, bearing in mind the solvent systems to be employed. For example, for polar aprotic solvents, such as dimethylformamide or N-methylpyrrolidone, polar aprotic side groups such as amides and ketones are appropriate. For protic solvents, e.g. water, acids or alcohols, ionizable side groups, e.g. pyridyl or sulfonate, might be considered.

The solubilizing substituent may also act to twist the main chain phenylene units out of planarity (although the main chain remains straight and not coiled). Phenylene pairs with substituents at the 2,2' positions will be twisted out of planarity by steric repulsion. Since planar phenylene chains pack more efficiently, a twisted chain will be more soluble. One means of solubilizing rigid-rod molecules is to provide adjacent phenylene pairs with substituents ortho with respect to the other phenylene of the pair. Even occasional 2,2' side groups will disrupt packing and enhance solubility. Another means of improving solubility is to decrease the order (increase the entropy) of the side groups, for example by a random copolymer with two or more different types of substituents. Other mechanisms of increasing solubility may also be possible.

Nonlimiting examples of G are: phenyl, biphenyl, naphthyl, phenanthryl, anthracenyl, benzyl, benzoyl, naphthoyl, phenoxy, phenoxyphenyl, phenoxybenzoyl, alkyl, alkyl ketone, aryl, aryl ketone, aralkyl, alkaryl, alkoxy, aryloxy, alkyl ester, aryl ester (esters may be C-bound or O-bound), amide, alkyl amide, dialkyl amide, aryl amide, diaryl amide, alkyl aryl amide, amides of cyclic amines such as piperidine, piperazine and morpholine (amides may be CO-bound or N-bound), alkyl ether, aryl ether, alkyl sulfides, aryl sulfides, alkyl sulfones, aryl sulfones, thioether, fluoro, trifluoromethyl, perfluoroalkyl, and pyridyl, where alkyl is a linear or branched hydrocarbon chain having between 1 and 30 carbon atoms, and aryl is any single, multiple or fused ring aromatic or heteroaromatic group having between 3 and 30 carbon atoms. Flourine-substituted analogs of the above-identified side groups may also be used.

$G_1$ and $G_2$, and/or $G_3$ and $G_4$ may be interconnected to form bridging groups. Nonlimiting examples of such groups and the monomer units that result are shown below:

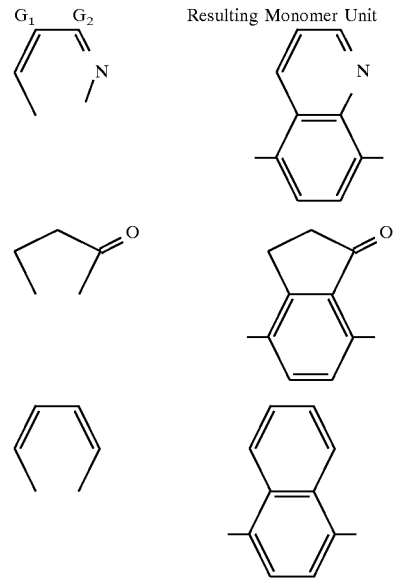

Solubilizing side groups G may also be oligomeric or polymeric groups. Using side groups which are functionally equivalent to the flexible polymer to be strengthened increases the compatibility of the rigid segments with the flexible segments. A nonlimiting example is the use of a macromonomer, denoted "$M_{oligo}$," bearing oligocaprolactam side groups G, as a comonomer with caprolactam in the preparation of poly(hexamethyleneadipamide-co-$M_{oligo}$).

For cases where the monomer unit of the macromonomer is unsymmetrical about the plane perpendicular to the polymer axis and centered on the monomer unit, for example if $G_1$ is benzoyl and G2, $G_3$, and $G_4$, are hydrogen, isomeric forms of the macromonomer exist. The monomers can link exclusively head-to-tail to form a regular structure. The monomers can also form a regular structure by linking exclusively head-to-head and tail-to-tail. Other more complicated structures and a random structure are also possible. The particular monomers and conditions used to form the macromonomer will determine the detailed structure. As used herein, structures (1), (2) and (3) represent all isomeric cases, either regular or random.

More than one type of monomer may be used to prepare the macromonomers of the present invention. Depending on the monomer used and the conditions of preparation, the resulting macromonomer may be a random copolymer or it may have additional order, as in a block, diblock, multiblock, or alternating copolymer. Copolymerization is a convenient way to adjust the number and type of side groups G.

It will sometimes be desirable to include 1,4-dichlorobenzene as a comonomer, so that some monomer units will be unsubstituted, i.e., $G_1=G_2=G_3=G_4=H$. The unsubstituted units will increase stiffness, but lower solubility. Unsubstituted monomer units will also lower cost.

Reactive End Groups

The reactive end groups, E, are chosen to allow copolymerization with the flexible polymer to be stiffened or strengthened. In one embodiment of the invention, an end group is interconnected with the main chain of the rigid-rod macromonomer by reacting a chemical moiety referred to herein as an "endcap" or "endcapper" during or after polymerization of the monomer units that form the main chain of the macromonomer.

Reactive end groups can be further derivatized to provide additional examples of end functionality E, as for example during deprotection, or transformation of one reactive group into another, for example reduction of a nitrile into an amine, or an aldehyde into an alcohol, or an amine into an imine. More than one type of end group may be present. For example, if three different endcappers are used during preparation of the macromonomer, a distribution of end groups will result.

The relative reactivity of endcapper and monomer must also be taken into account during macromonomer preparation. If the endcapper is significantly more reactive than the monomer it will be depleted before the monomer, resulting in some chains without end groups and an irregular molecular weight distribution. The endcapper may be added after the reaction has proceeded to a desired molecular weight, as determined for example by viscosity; however, in this case excess endcapper may be used, and there may be formation of some "endcapper dimer." If the endcapper is inexpensive, the dimer may be tolerated and, if necessary, removed in a later purification step.

It should be noted that impurities and side reactions will act to limit the molecular weight and will result in some of the end groups being different from the desired group E. It will often be the case that many chains are terminated at one, and to a lesser extent both, ends by non-reactive end groups derived from adventitious endcappers or side reactions. This will not usually detract from the utility of the rigid-rod macromonomers of the present invention. The small amount of macromonomer chains having a single reactive endgroup will still be able to participate in later processing. The even smaller amount with both ends non-reactive is not likely to macrophase separate due to its low concentration and affinity toward the larger amount of doubly terminated macromonomers.

It may be desirable to prepare macromonomers having several types of reactive end groups. This may be accomplished by adding several different endcappers during synthesis of the macromonomer. It may be desired that the different end groups have varying degrees of reactivity. It may also be desired that each macromonomer have only one reactive end group, the other being relatively inert. If two endcappers are used during macromonomer synthesis, typically a statistical distribution of end groups will result, consistent with the relative reactivities of the endcappers and the growing macromonomer chain. Such a statistical distribution may be separated by methods known in the art, for example chromatography, to yield substantially pure samples of macromonomers having two end groups, E and E'. Macromonomers with a single reactive end group and a single inert end group may be useful in addition polymerizations where crosslinking must be avoided.

If the macromonomer is prepared using a transition metal catalyst, and the synthesis proceeds through metallo-terminated chains as intermediates, the molecular weight of the resulting macromonomer may be controlled by the catalyst-to-monomer ratio. In this case the polymerization will cease when the number of chain ends (capped with catalyst) equals the number of catalyst molecules initially present. The $DP_n$ will equal twice the monomer to catalyst ratio. End groups E then may be introduced by adding reagents which displace the metallo end groups. The metallo-terminated macromonomer is thereby quenched. Introducing end groups by quenching avoids any problems of relative rates of endcapper and monomer.

A macromonomer bearing a particular end group, for example, an amine or alcohol, may be prepared by first endcapping or quenching with a precursor which is subsequently transformed into the desired end group. The precursor group need not be an amine or alcohol, e.g., and may be unrelated to the final end group except that an appropriate chemical transformation exists to convert the precursor to, e.g., an amine or alcohol. For example, a fluorobenzophenone precursor group can be converted into a variety of amines or alcohols by nucleophilic displacement of fluoride.

Amines form an important class of end groups. Amine-terminated macromonomers can be used with polyamides, polyimides, polyimidamides, polyureas, polyimines, and other polymers derived from bisamine monomers. Amine-terminated macromonomers can also be used with polymers not derived from bisamine monomers, such as epoxides and polyesters; in the latter case the macromonomer would be incorporated into the polyester chain via amide links. Preparation of the amine terminated macromonomers can involve protection/deprotection of the amine groups, for example as a succinimide, or an amide.

The following are nonlimiting examples of amine derived end groups: amino, aminoalkyl, aminoaryl, aminoalkaryl, aminoaralkyl, aniline, c-alkylaniline, N-alkylaniline, aminophenoxy, and aminobenzoyl. Other substituted and/or chemically protected aniline side groups may also be used. The following structures illustrate non-limiting examples of amine-derived end groups. Typical amines, amino alkyls, and amino aralkyls are given by the following structures (4a–4d):

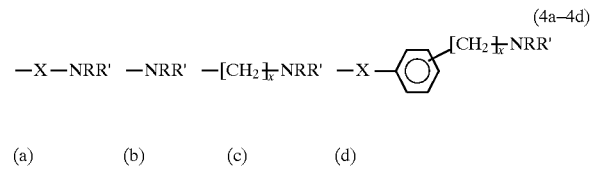

(4a–4d)

—X—NRR'   —NRR'   —[CH$_2$]$_k$—NRR'   —X—

(a)        (b)         (c)                (d)

where R and R' may be independently chosen from: hydrogen, alkyl, aryl, alkaryl, aralkyl, alkylketone, arylketone, alkylether or arylether, where alkyl and aryl are as defined above, x ranges from one to about twenty, and X is a difunctional group chosen from: nil, phenyleneoxy, ketophenylene, phenylenesulfone, —O—, —NH—, keto, —SO$_2$—, aryl, alkyl, alkaryl, or aralkyl. R and R' include bridging groups, such as —CH$_2$CH$_2$CH$_2$CH$_2$CH$_2$—, —CH$_2$CH$_2$OCH$_2$CH$_2$—, and —CH$_2$CH$_2$CH$_2$CO—. R and R' will often be used as protecting groups, to be removed at a later stage of processing, and as such include common amine and alcohol protecting groups, nonlimiting examples of which are: trimethylsilyl, trityl, tetrahydropyranyl, tosyl, methoxyisopropylidene, imide, imine, amide, ester, and the like.

Typical amino aryl end groups, E, have the structures (5a–5c):

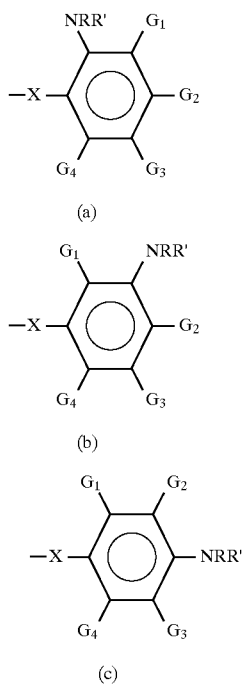

(5a–5c)

(a)

(b)

(c)

where X, R, R' and the groups $G_1$ through $G_4$ are as defined above. Aniline end groups have the above structure where X is nil and the G's are all hydrogen.

Aminophenoxyphenyl and aminobenzophenone end groups have the general structures (6a and 6b):

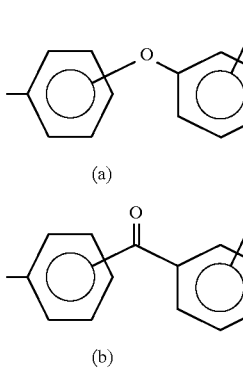

(6a–6b)

(a)

(b)

where R and R' are as defined above.

It should be noted that some endcappers can react to form dimers. The extent of such reactions is determined by the ratio of endcapper to monomer, and is usually very small. This is usually not of significance, however, certain endcappers, for example N-(4-chlorophenyl)-succinimide, will, when dimerized, form benzidine or benzidine derivatives, which are highly toxic. If such materials are used proper precautions should be taken. Where possible such materials should be avoided.

The imides comprise a second class of end groups. The maleimides are represented by the structures 4a–6b, where R and R' together equal the bridging group —COCH=CHCO—. Bismaleimides are commercially valuable in thermoset resins. Rigid-rod macromonomers with maleimide end groups are useful for strengthening conventional bismaleimide resins. They may also be used alone as novel bismaleimide resins containing rigid-rod elements. Other reactive imide end groups are contemplated by the present invention, including the nadimide end groups. Unreactive imides may also be used; succinimide may be used as a protected form of amine.

Closely related to the amines are the amides. In structures 4a–6b, if R or R'=—COalkyl or —COaryl, end groups are amides. If R or R'=—COCH=$CH_2$, the end groups are acrylamides. Amide functionalized macromonomers are also useful in reinforcing polyamides, such as nylon. Amide groups may react by transamination with the flexible polymer during polymerization or compounding.

Another important class of reactive end groups are alcohols and ethers. Diol-capped macromonomers may be used as comonomers with other diol monomers. Polyesters, polycarbonates, urethanes, and polyethers are nonlimiting examples of polymers prepared from diols. Alcohol macromonomers may also be used in non-diol derived polymers, for example, polyamides, where linkage to the macromonomer is through ester links. Both the amine macromonomers and the alcohol macromonomers may be used to replace dibasic monomers, in general, in condensation polymerizations.

Nonlimiting examples of alcohol-terminated macromonomers are: hydroxy, hydroxyalkyl, hydroxyaryl, hydroxyalkaryl, hydroxyaralkyl, phenol, C-alkylphenol, o-alkylphenol, hydroxyphenoxy, and hydroxybenzoyl. The following nonlimiting structures (7a–7d) illustrate exemplary alcohol end groups:

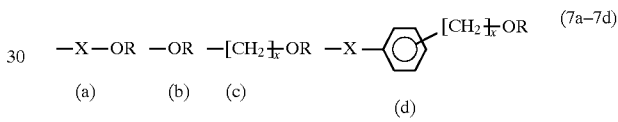

(7a–7d)

(a)   (b)   (c)   (d)

where R, x and X are as defined in the discussion following structures (4a–4d).

The following structures (8a–8c) are representative of phenolic end groups:

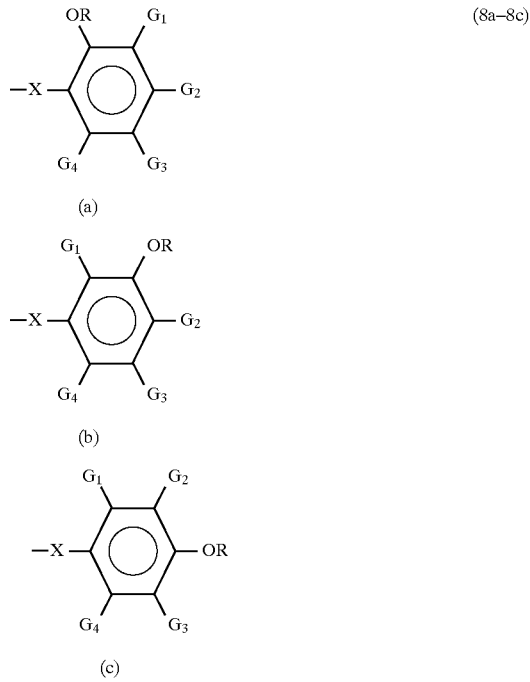

(8a–8c)

(a)

(b)

(c)

where $G_1$–$G_4$, R, and X are as defined above.

The following structures (9a–9c) are more specific examples of the above structures:

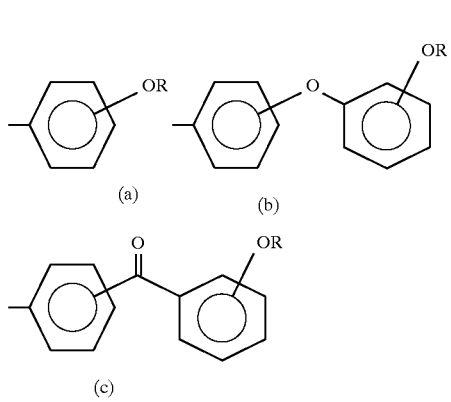

(9a–9c)

where R is as defined above.

For R=H, the structures (9a–9c) represent phenol, hydroxyphenoxyphenyl, and hydroxybenzophenone end groups, respectively. For R=ketoalkyl or ketoaryl, the structures (9a–9c) are phenylesters. R may contain additional reactive groups, such as acrylate or vinyl. In structures 7a through 9c, for R=—COCH=CH$_2$ the end groups are acrylates, for R=—CH=CH$_2$ the end groups are vinyl ethers.

Carbonyl-containing reactive end groups including acetyl, formyl, carboxy, ester, amide, acrylate, ketoalkyl and ketoaryl are represented by the structures (10a–10d) where Y is CH$_3$, H, OH, OR, NRR', vinyl, alkyl and aryl respectively, and G$_1$–G$_4$ and X are as defined above. Amides may be C- or N-bound; see structures 4a–6b above

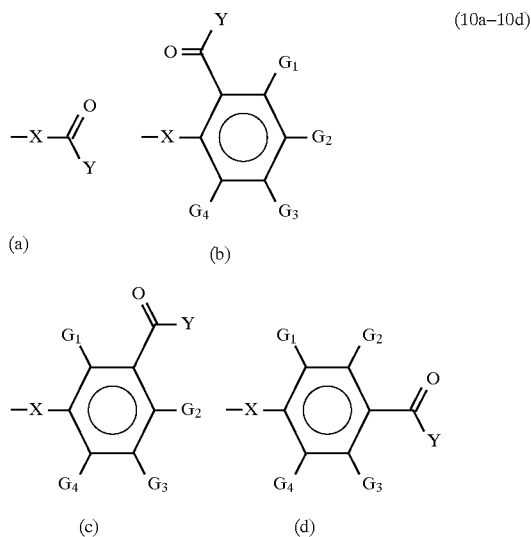

(10a–10d)

Macromonomers of the present invention having carboxy end groups may be used to reinforce polyesters, polycarbonates, and polyamides.

Acetylene end groups have the structures (11a–11d) where Y is —CCH. Olefin end groups have the structures (11a–11d) where Y is —CH=CH$_2$. Halide, cyano, cyanate, and isocyanate end groups have the structures (11a–11d) where Y is -halogen, —CN, —OCN and —NCO respectively.

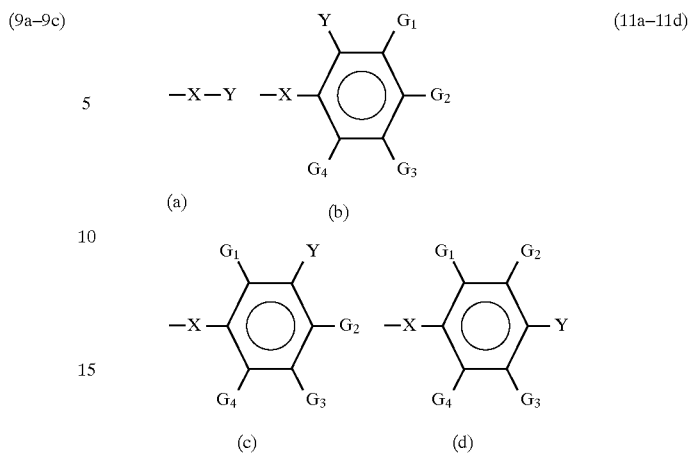

(11a–11d)

Reactive end groups may also be strained ring compounds including epoxides, biphenylenes and benzocyclobutenes.

In situations where the reactive end groups E are reactive with each other, both the end groups E and the groups on the flexible polymer or monomer with which they are ultimately to react should be selected so that the relative rates of reaction are approximately equal. This will enhance the randomness of the distribution of the macromonomer within the final polymer.

When the rigid-rod macromonomers of the present invention are used as pre-polymerization additives, they are preferably added in an amount such that W$_r$ ranges from 1 percent to 60 percent, i.e., the rigid-rod macromonomers make up from 1 percent to 60 percent of the weight of the resulting polymeric material. Such a range takes into account the trade off between increased cost and decreased processability that results as the value of W$_r$ increases in magnitude. In practice, it is desirable to experimentally determine the optimal weight fraction required for particular applications.

In certain circumstances, it may be desirable for W$_r$ to exceed 60 percent of the total weight of the copolymeric material. For instance, when the rigid-rod macromonomers of the present invention are used alone as thermosetting resins, W$_r$ can approach the limiting value of 100 percent, depending on the size, frequency, and orientation of the crosslinking groups formed during curing. In addition, suitable endcapped macromonomers could be utilized to prepare new rigid-rod copolymers wherein all of the segments are rigid. For instance, if a macromonomer with amino end-groups were reacted with pyromellitic dianhydride (PMDA), the resulting copolymer would be a rigid-rod after complete imidization. The polyamic acid prepolymer should retain reasonable processability and could be fabricated into desirable shapes before effecting imidization to the final rigid-rod polymer.

There will also be an optimal range for L$_r$, typically between 8 and 500 repeat units, beyond which additional increases in length will have little further effect on strength or stiffness but will reduce processability. Optimal ranges for both W$_r$ and L$_r$ can be readily determined by one skilled in the art.

The aspect ratio of the macromonomers incorporated into copolymers also affects the physical properties of the copolymers, particularly the processability thereof. The aspect ratio of a macromonomer is defined to be the length to diameter ratio of the smallest diameter cylinder which will enclose the macromonomer segment, including half the length of the terminal connecting bonds, including hydrogen but not any attached side groups, such that the axis of the cylinder is parallel to the connecting bonds in the straight segment.

For rigid-rod polyphenylenes, and aza analogs, the aspect ratio is approximately equal to the $DP_n$, because the phenylene monomer unit has an aspect ratio of about one.

When the average aspect ratio of the macromonomers is less than about 7 or 8, the macromonomers typically do not impart the desired strength and stiffness into the final polymer. As the aspect ratio is increased, the mechanical properties of the reinforced polymer improve. All other factors being equal, a longer rigid-rod segment will provide a greater increase in stiffness than a shorter rigid-rod segment. This is true for reinforcement of any geometrical type of polymer, e.g., linear, branched, crosslinked, and so forth. It is known in the art that for conventional fiber-containing composites mechanical properties improve rapidly up to aspect ratios of about 100, after which there are lesser improvements. A similar situation has been found to exist for rigid-rod macromonomers.

Although mechanical properties of the polymers improve as the aspect ratio increases, processing becomes more difficult. Viscosities of polymer solutions are dependent on the $DP_n$ of the polymer. Viscosities of rigid-rod polymers increase much more rapidly with $DP_n$ than viscosities of flexible polymers. Similarly, melt viscosities of flexible polymers reinforced with rigid-rod polymers increase with the $DP_n$ of the rigid segments, making thermal processing more difficult as $DP_n$ increases.

There is generally a trade-off between improved mechanical properties and difficulty of processing, resulting in an optimal aspect ratio and $DP_n$ for the rigid-rod macromonomers. For example, if it is desired to increase the modulus of a flexible polymer reinforced with rigid-rod macromonomers, the aspect ratio of the macromonomer could be increased, but the melt and solution viscosity will increase and solubility of the rigid-rod macromonomer will decrease, making processing and preparation more difficult. $DP_n$'s of about 100 are often optimal; however, higher or lower $DP_n$'s may sometimes be desirable.

The following procedures provide three exemplary methods for preparing the rigid-rod macromonomers of the present invention, an exemplary method of preparing succinimide-protected amines, and other synthetic methods used in the present invention. More specific methods are given below in the Examples, which refer to the General Procedures. The choices and amounts of reagents, temperatures, reaction times, and other parameters are illustrative, but are not considered limiting in any way. Other approaches are contemplated by, and within the scope of, the present invention.

It will also be recognized by one skilled in the art that for any given procedure certain functionalities will not be tolerated. For example, in General Procedures I–III protic side groups, end groups, solvents, or any source of acidic protons are not tolerated. Other procedures, e.g., that of Example 67 using a palladium catalyst, will tolerate protic groups and solvents. As a second example, nickel catalyzed couplings are known to be sensitive to nitro groups and ortho-dihalo groups.

For the nickel catalyzed coupling reactions used here, many variations on catalyst composition, accelerators, solvent, reducing agent, order of addition, and the like are possible. For example, phosphines other than triphenylphosphine have been used with nickel coupling catalysts, including triethylphosphine and bis(diphenylphosphino)ethane; electrochemical reduction has been used as an alternative to zinc; accelerators have included chloride, bromide, iodide, and aromatic nitrogen heterocycles such as 2,2'-bipyridine; and solvents have included ethers, acetone, dimethylformamide, and acetonitrile.

General Procedure —I. (Preparation of Macromonomer by Simultaneous Addition of Monomer and Endcapper)

Anhydrous bis(triphenylphosphine) nickel(II) chloride (0.25 g; 0.39 mmol), triphenylphosphine (0.60 g; 2.29 mmol), sodium iodide (0.175 g, 1.17 mmol), and 325 mesh activated zinc powder (approximately 1.5 mmol / mmol monomer) are placed into a 25 ml flask under an inert atmosphere along with 7 ml of anhydrous N-methylpyrrolidinone (NMP). This mixture is stirred for about 10–20 minutes, leading to a deep-red coloration. A solution of between 3–20 mmol of monomer and between about 0.3 to 2.5 mmol endcapper in 8 ml of anhydrous NMP is then added by syringe. After stirring for about 12–60 hours at 50°–60° C., the resulting viscous solution is poured into 100 ml of 1 molar hydrochloric acid in ethanol to dissolve the excess zinc metal and to precipitate the macromonomer. This suspension is filtered and the precipitate triturated with acetone and dried to afford a light yellow to white powder in 40–99% yield.

General Procedure —II. (Preparation of Macromonomer by Slow Addition of Endcapper to Monomer)

Anhydrous bis(triphenylphosphine) nickel(II) chloride (0.25 g, 0.39 mmol), triphenylphosphine (0.60 g; 2.29 mmol), sodium iodide (0.175 g, 1.17 mmol), and 325 mesh activated zinc powder (approximately 1.5 mmol / mmol monomer) are placed into a 25 ml flask under an inert atmosphere along with 7 ml of anhydrous N-methylpyrrolidinone (NMP). This mixture is stirred for about 10–20 minutes, leading to a deep-red coloration. A solution of between 3–20 mmol of monomer in 8 ml of anhydrous NMP is then added all at once by syringe, and between 0.3 to 2.5 mmol endcapper in 5 ml of anhydrous NMP is then added dropwise by syringe over a period ranging from about 15 to about 60 minutes with the reaction mixture held at 50°–60° C. After stirring for about 12–60 hours, the resulting viscous solution is poured into 100 ml of 1 molar hydrochloric acid in ethanol to dissolve the excess zinc metal and to precipitate the macromonomer. This suspension is filtered and the precipitate triturated with acetone and dried to afford a light yellow to white powder in 40–99% yield.

General Procedure —III. (Preparation of Macromonomer by Adding Endcapper to Monomer at End of Reaction)

Anhydrous bis (triphenylphosphine) nickel (II) chloride (0.25 g, 0.39 mmol), triphenylphosphine (0.60 g; 2.29 mmol), sodium iodide (0.175 g, 1.17 mmol), and 325 mesh activated zinc powder (approximately 1.5 mmol / mmol monomer) are placed into a 25 ml flask under an inert atmosphere along with 7 ml of anhydrous N-methylpyrrolidinone (NMP). This mixture is stirred for about 10–20 minutes, leading to a deep-red coloration. A solution of between 3–20 mmol of monomer in 8 ml of anhydrous NMP is then added all at once by syringe and the reaction mixture brought to 50°–60° C. After a period ranging from about 15 minutes to about 24 hours (depending on the reactivity of the monomer), a large excess (at least about 5–10 mmol) of endcapper is then added by syringe. Typically the color of the reaction mixture will become green upon addition of the monomer and then evolve through orange and then back to red as the monomer is consumed. The endcap is optimally added just as the reaction begins to develop the orange coloration. After stirring for about 12–60 hours, the resulting viscous solution is poured into 100 ml of 1 molar hydrochloric acid in ethanol to dissolve the excess zinc metal and to precipitate the macromonomer. This suspension is filtered and the precipitate triturated with acetone and dried to afford a light yellow to white powder in 40–99% yield.

The above procedures I–III describe macromonomer formation by reductive coupling of monomer precursors, e.g., substituted 1,4-dihaloaromatic compounds, in the presence of a catalyst, and reaction with endcappers.

For the nickel catalyzed coupling reactions described in General Procedures I–III, it is believed that before quenching or workup, the nickel catalyst resides at the end of the chain, and on completion of reaction functions as a chain terminator. Therefore, the length of the macromonomer chain will be largely determined by the molar ratios of monomer (U), endcapper (E) and catalyst (C):

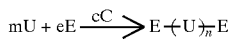

where m, e and c are the number of moles of monomer, endcapper and catalyst, respectively.

Those skilled in the art will recognize that the $DP_n$ at the completion of the macromonomer-forming reaction can be calculated using the Carothers equation. Assuming no chain limiting impurities, equal reactivity of monomer and endcapper, and that end groups E are not counted when calculating $DP_n$, the Carothers equation for General Procedures I and II simplifies to:

$$DP_n = 2m/(e+c)$$

Procedure III largely depends upon quenching the nickel-terminated polymer chains with an excess of endcapper so the degree of polymerization does not depend on e (because initially e=0), and thus:

$$DP_n = 2m/c$$

Methods for calculating required ratios of monomer, endcapper, catalyst, etc. given a desired $DP_n$ are known in the art for various types of polymerization reactions and conditions. It is often useful to experimentally determine the extent of reaction, p, by preparing a polymer in the absence of endcapper and measuring $DP_n$. The extent of reaction p is then given by:

$$p = 1 - 1/DP_n$$

This experimentally determined p may then be used by methods known in the art to calculate the molar amounts of monomer and endcapper required.

Of course, $DP_n$ or any other property, such as viscosity, may be adjusted by trial and error, varying ratios of monomer, endcapper and catalyst experimentally to identify the desired range.

General Procedure —IV. (Preparation of succinimide protected amines)

The dry amine (0.5 mol) and succinic anhydride (0.5 mol) are dissolved in $2_L$ dry toluene. Catalyst, p-toluenesulfonic acid (0.01 mol), is then added and the mixture is held at reflux for 24 hours, using a Dean-Stark trap to collect water. After cooling, the product is precipitated with diethyl ether, filtered, washed with ether and dried.

General Procedure —V. (Removal of protecting groups)

In the cases where the functional end group is protected as an imide, amide, or ester, the protecting groups are removed as follows: The protected macromonomer is suspended in 25 ml of 10% HCl in ethanol and heated to reflux for six to twelve hours. This mixture is neutralized with sodium hydroxide, filtered, washed and dried. Further purification by dissolution and precipitation by adding a non-solvent may be effected.

Preparation of 2,5-Dichlorobenzoyl Compounds 2,5-dichlorobenzoyl-containing compounds (e.g. 2,5-dichlorobenzophenones and 2,5-dichlorobenzamides) can be readily prepared from 2,5-dichlorobenzoylchloride. Pure 2,5-dichlorobenzoylchloride is obtained by vacuum distillation of the mixture obtained from the reaction of commercially available 2,5-dichlorobenzoic acid with a slight excess of thionyl chloride in refluxing toluene. 2,5-dichlorobenzophenones (2,5-dichlorobenzophenone, 2,5-dichloro-4'-methylbenzophenone, 2,5-dichloro-4'-methoxybenzophenone, and 2,5-dichloro-4'-phenoxy-benzophenone) are prepared by the Friedel-Crafts benzoylations of benzene and substituted benzenes (e.g. toluene, anisole, diphenyl ether), respectively, with 2,5-dichlorobenzoylchloride at 0°–5° C. using 2–3 mol equivalents of aluminum chloride as a catalyst. The solid products obtained upon quenching with water are purified by recrystallization from toluene/hexanes. 2,5-dichlorobenzoylmorpholine and 2,5-dichlorobenzoylpiperidine are prepared from the reaction of 2,5-dichlorobenzoylchloride and either morpholine or piperidine, respectively, in toluene with pyridine added to trap the HCl that is evolved. After washing away the pyridinium salt and any excess amine, the product is crystallized from the toluene solution.

Preparation of Activated Zinc Powder

Activated zinc powder is obtained after 2–3 washings of commercially available 325 mesh zinc dust with 1 molar hydrogen chloride in diethyl ether (anhydrous) and drying in vacuo or under inert atmosphere for several hours at about 100°–120° C. This material should be used immediately or stored under an inert atmosphere away from oxygen and moisture.

The following specific examples are illustrative of the present invention, but are not considered limiting thereof in any way.

EXAMPLE 1

Preparation of a macromonomer of the structure (1), where $G_1$ is p-toluyl ($-COC_6H_4-4-CH_3$), $G_2$ through $G_4$ are hydrogen, E is 3-carbomethoxyphenyl ($-C_6H_4(COOCH_3)$), and $DP_n \approx 7$.

Anhydrous bis(triphenylphosphine)nickel(II) chloride (0.505 g; 0.77 mmol), triphenylphosphine (0.40 g; 1.53 mmol), sodium iodide (0.175 g, 1.17 mmol), and 325 mesh activated zinc powder (1.0 g, 15.3 mmol) were placed into a 25 ml flask under an inert atmosphere along with 7 ml of anhydrous N-methylpyrrolidinone (NMP). This mixture was stirred for about 10–20 minutes, leading to a deepred coloration. A solution of 2,5-dichloro-4'-methylbenzophenone (1.84 g; 6.94 mmol) and methyl-3-chlorobenzoate (0.32 g; 1.88 mmol) in 8 ml of anhydrous NMP was then added by syringe. After stirring for about 18 hours at 50° C., the reaction mixture was poured into 100 ml of 1 molar hydrochloric acid in ethanol to dissolve the excess zinc metal and to precipitate the macromonomer. This suspension was filtered and the precipitate triturated with acetone and dried to afford a 42% yield of the macromonomer. Analysis of the macromonomer by size exclusion chromatography (SEC) indicated a weight average molecular weight (relative to polystyrene) of 14,000 with a polydispersity of 1.4. Proton nuclear magnetic resonance ($^1$H NMR; 500 MHz) spectroscopy indicated that the macromonomer consisted of a monomer-to-endcap ratio of 8.8:1.

EXAMPLE 2

Preparation of a macromonomer of the structure (1), where $G_1$ is p-toluyl, $G_2$ through $G_4$ are hydrogen, E is 3-carbomethoxyphenyl, and $DP_n \approx 7$.

The procedure of Example 1 was followed, except that an additional 0.33 g of methyl-3-chlorobenzoate was added to the reaction mixture after about 3 hours at 50° C. After 4.5 hours, the reaction mixture was worked up as in Example 1 to afford a 48% yield of the macromonomer. SEC analysis (relative to polystyrene) indicated $M_w$=15,600 and polydispersity of 1.5.

EXAMPLE 3

Preparation of a macromonomer of the structure (1), where $G_1$ is p-toluyl, $G_2$ through $G_4$ are hydrogen, E is 3-carbomethoxyphenyl, and $DP_n \approx 7$.

The procedure of Example 2 was followed, except that the additional 0.33 g of methyl-3-chlorobenzoate was added after about 18 hours. After 24 hours, the reaction mixture was worked up as before to afford a 43% yield of the macromonomer. SEC analysis (relative to polystyrene) indicated $M_w$=14,000 and polydispersity of 1.4.

EXAMPLE 4

Preparation of a macromonomer of the structure (1), where $G_1$ is p-toluyl, the $G_2$ through $G_4$ are hydrogen, E is 3-carbomethoxyphenyl, and $DP_n \approx 16$.

General Procedure I was followed, where the monomer was 2,5-dichloro-4'-methylbenzophenone (2.55 g; 9.62 mmol), the endcapper was methyl-3-chlorobenzoate (0.16 g; 0.96 mmol), and 1.0 g (15.3 mmol) of zinc was used. After 18 hours the reaction was worked up to afford a 69% yield of the macromonomer. SEC analysis (relative to polystyrene) indicated $M_w$=29,500 and polydispersity of 3.0.

EXAMPLE 5

Preparation of a macromonomer of the structure (1), where $G_1$ is p-toluyl, $G_2$ through $G_4$ are hydrogen, E is 3-carbomethoxyphenyl, and $DP_n \approx 30$.

General Procedure I was followed, where the monomer was 2,5-dichloro-4'-methylbenzophenone (5.11 g; 19.27 mmol), the endcapper was methyl-3-chlorobenzoate (0.16 g; 0.96 mmol), and 2.0 g (39.7 mmol) of zinc was used. After 18 hours the reaction was worked up to afford a greater than 90% yield of the macromonomer. SEC analysis (relative to polystyrene) indicated $M_w$=54,000 and polydispersity of 3.9. Proton nuclear magnetic resonance ($^1$H NMR; 500 MHz) spectroscopy indicated that the macromonomer consisted of a monomer-to-endcap ratio of 34:1.

EXAMPLE 6

Preparation of a macromonomer of the structure (1), where $G_1$ is p-toluyl, $G_2$ through $G_4$ are hydrogen, E is 3-carbomethoxyphenyl, and $DP_n \approx 30$.

The procedure of Example 5 was followed, but an additional 0.16 g of the methyl-3-chlorobenzoate endcapper was added to the reaction mixture after 6 hours. After 18 hours the reaction was worked up to afford a 95% yield of the macromonomer. SEC analysis (relative to polystyrene) indicated $M_w$=66,000 and polydispersity of 3.8.

EXAMPLE 7

Preparation of a macromonomer of the structure (1), where $G_1$ is benzoyl, $G_2$ through $G_4$ are hydrogen, E is 3-carbomethoxyphenyl, and $DP_n \approx 16$.

Anhydrous bis (triphenylphosphine) nickel (II) chloride (5.04 g; 7.7 mmol), triphenylphosphine (12 g; 45.75 mmol), sodium iodide (3.5 g, 23.35 mmol), and 325 mesh activated zinc powder (20 g, 306 mmol) were placed into a 500 ml round-bottom flask under an inert atmosphere along with 140 ml of anhydrous N-methylpyrrolidinone (NMP). This mixture was stirred for about 10–20 minutes, leading to a deep-red coloration. A solution of 2,5-dichlorobenzophenone (48.36 g; 193 mmol) and methyl-3-chlorobenzoate (3.28 g; 19.2 mmoi) in 160 ml of anhydrous NMP was then added. After stirring for about 3 days at 50° C., the viscous reaction mixture was poured into 700 ml of 1 molar hydrochloric acid in ethanol to dissolve the excess zinc metal and to precipitate the macromonomer. This suspension was filtered and the precipitate triturated with acetone and dried to afford a 62% yield of the macromonomer. Analysis of the macromonomer by SEC indicated a weight average molecular weight (relative to polystyrene) of 37,000 with a polydispersity of 1.9.

EXAMPLE 8

Preparation of a macromonomer of the structure (1), where $G_1$ is p-toluyl, $G_2$ through $G_4$ are hydrogen, E is 3-carbomethoxyphenyl and $DP_n \approx 10$.

General Procedure III was followed, where the monomer was 2,5-dichloro-4'-methylbenzophenone (2.55 g, 9.62 mmol) and the endcapper, methyl-3-chlorobenzoate (0.164 g; 0.96 mmol), was added after a period of 25 minutes. After stirring for about 18 hours, the viscous reaction mixture was poured into 100 ml of 1 molar hydrochloric acid in ethanol to dissolve the excess zinc metal and to precipitate the macromonomer. This suspension was filtered and the precipitate triturated with acetone and dried to afford a 66% yield of the macromonomer. Analysis of the macromonomer by SEC indicated a weight average molecular weight (relative to polystyrene) of 19,000 with a polydispersity of 2.1.

EXAMPLE 9

Preparation of a macromonomer of the structure (1), where $G_1$ is p-anisoyl, $G_2$ through $G_4$ are hydrogen, E is 3-acetylphenyl, and $DP_n \approx 16$.

General Procedure II is followed, where the monomer is 2,5-dichloro-4'-methoxybenzophenone (2.4 g, 8.37 mmol) and the endcapper, 3-chloroacetophenone (119 mg, 0.77 mmol), is added over about 15 minutes to yield the acetyl-functionalized macromonomer.

EXAMPLE 10

Preparation of a macromonomer of the structure (1), where $G_1$ is p-anisoyl, $G_2$ through $G_4$ are hydrogen, E is 4-acetylphenyl, and $DP_n \approx 41$.

General Procedure II is followed, where the monomer is 2,5-dichloro-4'-methoxybenzophenone (4.8 g, 16.74 mmol) and the endcapper is 4-chloroacetophenone (63 mg, 0.44 mmol), which is added dropwise over a period of about 30 minutes, to yield the acetyl-functionalized macromonomer.

EXAMPLE 11

Preparation of a macromonomer of the structure (1), where $G_1$ is benzoyl, $G_2$ through $G_4$ are hydrogen, E is 4-acetylphenyl, and $DP_n \approx 22$.

General Procedure III is followed, where the monomer is 2,5-dichlorobenzophenone (1.1 g, 4.38 mmol) and the endcapper is 4-chloroacetophenone (1 ml, 7.7 mmol), which is added all at once after a period of 20 minutes, to yield the acetyl-functionalized macromonomer.

EXAMPLE 12

Preparation of a macromonomer of the structure (1), where $G_1$ is benzoyl, $G_2$ through $G_4$ are hydrogen, E is 3-formylphenyl, and $DP_n \approx 11$.

General Procedure II is followed, where the monomer is 2,5-dichlorobenzophenone (1.1 g, 4.38 mmol) and the endcapper is 3-chlorobenzaldehyde (70 mg, 0.5 mmol) in 5 ml of anhydrous NMP, which is added over a period of about 30 minutes, to yield the formyl-functionalized macromonomer.

EXAMPLE 13

Preparation of a macromonomer of the structure (1), where $G_1$ is benzoyl, $G_2$ through $G_4$ are hydrogen, E is 3-carbophenoxyphenyl, and $DP_n \approx 13$.

General Procedure I is followed, where the monomer is 2,5-dichlorobenzophenone (2.89 g; 11.5 mmol) and the endcapper is phenyl-3-chlorobenzoate (0.40 g, 1.72 mmol) to yield the ester-functionalized macromonomer.

Phenyl-3-chlorobenzoate is prepared by reacting 3-chlorobenzoyl chloride with phenol in toluene with some pyridine (1 mol equivalent per acid chloride) to trap the HCl that evolves. After aqueous extraction of the pyridinium salt and any excess starting materials, the product is crystallized from the toluene solution.

EXAMPLE 14

Preparation of a macromonomer of the structure (1), where $G_1$ is benzoyl, $G_2$ through $G_4$ are hydrogen, E is 4-(N,N-dimethylcarbamyl)phenyl, and $DP_n \approx 17$.

The procedure of Example 13 is followed, but the endcapper is 4-chloro-N,N-dimethylbenzamide (0.20 g, 1.09 mmol) to yield the amido-functionalized macromonomer. 4-Chloro-N,N-dimethylbenzamide is prepared by reacting 4-chlorobenzoyl chloride with dimethylamine in toluene with some pyridine (1 mol equivalent per acid chloride) to trap the HCl that is evolved. After aqueous extraction of the pyridinium salt and any excess starting materials, the product is crystallized from the toluene solution.

EXAMPLE 15

Preparation (1), where $G_1$ is benzoyl, $G_2$ through $G_4$ are hydrogen, E is 4-acrylylphenyl (4-$C_6H_4COCHCH_2$), and $DP_n \approx 28$.

The procedure of Example 13 is followed, but the endcapper is 4'-chloro-3-dimethylaminopropiophenone (0.10 g, 0.47 mmol) to yield the ketone-functionalized macromonomer. The product has structure 1, where $G_1$ is benzoyl, $G_2$ through $G_4$ are hydrogen, E is 4'-(3-di-methyl-aminopropionyl) phenyl, and $DP_n \approx 28$. This oligomer can be converted to the more useful acrylyl-terminated form by thermally induced loss of dimethylamine. 4'-Chloro-3-dimethylaminopropiophenone is prepared by treating 4'-chloro-3-dimethylaminopropiophenone hydrochloride with aqueous base to remove the HCl. The free amine is extracted into diethyl ether and recovered by evaporation of the solvent. The hydrochloride salt is prepared by the method of Maxwell in *Org. Synth. Coll.* Vol. III, 305–306. Thus, a mixture of 4-chloroace-tophenone, dimethylamine hydrochloride, and paraformaldehyde is refluxed for 2–4 hours in 95% ethanol with a small amount of added hydrochloric acid. The solid product is obtained after adding acetone and cooling overnight.

EXAMPLE 16

Preparation of a macromonomer of the structure (1), where $G_1$ is benzoyl, $G_2$ through $G_4$ are hydrogen, E is 4-cyanophenyl, and $DP_n \approx 34$.

General Procedure II is followed, where the monomer is 2,5-dichlorobenzophenone (2.89 g; 11.5 mmol) and the endcapper is 4-chlorobenzonitrile (41 mg, 0.3 mmol) to yield the cyano-functionalized macromonomer. 3-Chlorophenyl vinyl ketone is prepared by thermolysis of 4'-chloro-3-dimethylaminopropiophenone hydrochloride (see Example 15).

EXAMPLE 17

Preparation of a macromonomer of the structure (1), where $G_1$ is benzoyl, $G_2$ through $G_4$ are hydrogen, E is 4-(napthalic-1,8-dianhydride), and $DP_n \approx 20-25$.

The procedure of Example 11 is followed, where the endcapper is 4-bromo-1,8-naphthalic anhydride (1.5 g, 5.41 mmol) in 10 ml of anhydrous NMP, which is added all at once after a period of 20 minutes, to yield the anhydride-functionalized macromonomer.

EXAMPLE 18

Preparation of a macromonomer of the structure (1), where $G_1$ is benzoyl, $G_2$ through $G_4$ are hydrogen, E is 3-carboxyphenyl, and $DP_n \approx 20-25$.

The procedure of Example 11 is followed, where the endcapper is 3-iodotoluene (1 ml, 7.79 mmol), which is added all at once after a period of 30 minutes, to yield the methyl-functionalized macromonomer. The product has structure 1, where $G_1$ is benzoyl, $G_2$ through $G_4$ are hydrogen, E is 3-tolyl, and $n \approx 20-25$. This oligomer can be converted to the more useful carboxy-terminated form by oxidation.

EXAMPLE 19

Preparation of a macromonomer of the structure (1), where $G_1$ is benzoyl, $G_2$ through $G_4$ are hydrogen, E is 4-acrylylphenyl, and $DP_n \approx 20-25$.

The procedure of Example 11 is followed, where the endcapper is 4-chlorophenyl vinyl ketone (1 ml, 7.79 mmol), which is added all at once after a period of 15 minutes, to yield the acrylyl-functionalized macromonomer.

EXAMPLE 20

Preparation of a macromonomer of the structure (1), where $G_1$ is benzoyl, $G_2$ through $G_4$ are hydrogen, E is methyl, and $DP_n 20-25$.

The procedure of Example 11 is followed, where the endcapper is methyl iodide (0.5 ml, 8.0 mmol), which is added all at once after a period of 90 minutes, to yield the methyl-functionalized macromonomer. This oligomer can be converted to the more useful carboxy-terminated form by oxidation. The resulting product has structure 1, where $G_1$ is benzoyl, the remaining G's are hydrogen, E is carboxy, and $n \approx 20-25$.

EXAMPLE 21

Preparation of a macromonomer of the structure (1), where $G_1$ is benzoyl, $G_2$ through $G_4$ are hydrogen, E is cyano, and $DP_n \approx 20-25$.

The procedure of Example 11 is followed, where the endcapper is sodium cyanide (0.5 g; 10.2 mmol) in 1 ml of anhydrous NMP, which is added all at once after a period of 30 minutes, to yield the cyano-functionalized macromonomer.

EXAMPLE 22

Preparation of a macromonomer of the structure (1), where $G_1$ is benzoyl, $G_2$ through $G_4$ are hydrogen, E is N-succinimido, and $DP_n \approx 20$–25.

The procedure of Example 11 is followed, where the endcapper is N-bromosuccinimide (NBS) (1 g, 5.6 mmol), which is added all at once after a period of 30 minutes, to yield the succinimido-functionalized macromonomer. This oligomer can be converted to the more useful amino-terminated form by acidic hydrolysis. The resulting product has structure 1, where $G_1$ is benzoyl, the remaining G's are hydrogen, E is amino, and n≈20–25.

EXAMPLE 23

Preparation of a macromonomer of the structure (1), where $G_1$ is benzoyl, $G_2$ through $G_4$ are hydrogen, E is acetyl, and $DP_n \approx 20$–25.

The procedure of Example 11 is followed, where the endcapper is acetyl chloride (0.5 ml, 7.0 mmiol), which is added all at once after a period of 90 minutes, to yield the acetyl-functionalized macromonomer.

EXAMPLE 24

Preparation of a macromonomer of the structure (1), where $G_1$ is benzoyl, $G_2$ through $G_4$ are hydrogen, E is acrylyl, and $DP_n \approx 20$–25.

Procedure of Example 11 is followed, where the endcapper is acryloyl chloride (0.5 ml, 6.2 mmol), which is added all at once after a period of 90 minutes, to yield the acrylyl-functionalized macromonomer.

EXAMPLE 25

Preparation of a macromonomer of the structure (1), where $G_1$ is benzoyl, $G_2$ through $G_4$ are hydrogen, E is 5-carbethoxypentanoyl ($COCH_2CH_2CH_2CH_2CO_2CH_2CH_3$) and $DP_n \approx 20$–25.

The procedure of Example 11 is followed, where the endcapper is adipoyl chloride (1 ml, 6.9 mmol), which is added all at once after a period of 90 minutes, to yield the adipyl-functionalized macromonomer.

EXAMPLE 26

Preparation of a macromonomer of the structure (1), where $G_1$ is carbonylmorpholine ($-(CO)NCH_2CH_2OCH_2CH_2$), $G_2$ through $G_4$ are hydrogen, E is 4-acetylphenyl, and $DP_n \approx 20$–25.

General Procedure III is followed, where the monomer is 2,5-dichlorobenzoylmorpholine (1.1 g, 4.23 mmol) and the endcapper is 4-chloroacetophenone (1 ml, 7.7 mmol), which is added all at once after a period of 18 hours, to yield the acetyl-functionalized macromonomer.

EXAMPLE 27

Preparation of a macromonomer of the structure (1), where $G_1$ is carbonylmorpholine, $G_2$ through $G_4$ are hydrogen, E is 3-carbophenoxyphenyl, and $DP_n \approx 20$–25.

The procedure of Example 26 is followed, where the endcapper is phenyl-3-chlorobenzoate (1.5 g, 6.4 mmol), which is added all at once after a period of 8 hours, to yield the ester-functionalized macromonomer.

EXAMPLE 28

Preparation of a macromonomer of the structure (1), where $G_1$ is carbonylmorpholine, $G_2$ through $G_4$ are hydrogen, E is 4-carbethoxyphenyl, and $DP_n \approx 21$.

General Procedure I is followed, where the monomer is 2,5-dichlorobenzoylmorpholine (2.5 g, 10.0 mmol) and the endcapper is ethyl-4-chlorobenzoate (0.1 ml, 0.64 mmol) to yield the ester-functionalized macromonomer.

EXAMPLE 29

Preparation of a macromonomer of the structure (1), where $G_1$ is carbonylmorpholine, $G_2$ through $G_4$ are hydrogen, E is 4-acrylylphenyl, and $DP_n \approx 19$.

General Procedure II is followed, where the monomer is 2,5-dichlorobenzoylmorpholine (2.5 g, 10.0 mmol) and the endcapper is 4'-chloro-3-dimethylaminopropiophenone (0.15 g, 0.71 mmol) to yield the ketone-functionalized macromonomer. The product has structure (1), where $G_1$ is carbonylmorpholine, the remaining G's are hydrogen, E is 4'-(3-dimethylaminopropionyl)phenyl, and n≈20–25. This oligomer can be converted to the more useful acrylyl-terminated form by thermally induced loss of dimethylamine.

EXAMPLE 30

Preparation of a macromonomer of the structure (1), where $G_1$ is 4-phenoxybenzoyl, $G_2$ through $G_4$ are hydrogen, E is 4-acetylphenyl, and $DP_n \approx 27$.

General Procedure I is followed, where the monomer is 2,5-dichloro-4'-phenoxybenzophenone (5.0 g, 14.6 mmol) and the endcapper is 4-chloroacetophenone (0.1 ml, 0.77 mmol) to yield the acetyl-functionalized macromonomer.

EXAMPLE 31

Preparation of a macromonomer of the structure (1), where $G_1$ is 4-phenoxybenzoyl, $G_2$ through $G_4$ are hydrogen, E is 3-carbophenoxyphenyl, and $DP_n \approx 19$.

The procedure of Example 30 is followed, where the endcapper is phenyl-3-chlorobenzoate (0.30 g, 1.3 mmol) to yield the ester-functionalized macromonomer.

EXAMPLE 32

Preparation of a macromonomer of the structure (1) where $G_1$ is benzoyl, $G_2$ through $G_4$ are hydrogen, E is 2-(4'-aminobenzophenone), and $DP_n \approx 16$.

General Procedure I is followed, where the monomer is 2,5-dichlorobenzophenone (11.5 mmol) and the endcapper is 2-chloro-4'-(N-succinimido)benzophenone (1.15 mmol) (prepared in the manner described below). The resulting macromonomer is in the protected succinimide form. The free amine is obtained by refluxing the succinimide with 25 ml of 10% HCl in ethanol for six hours, followed by neutralization with sodium hydroxide, and extraction into methylene chloride. The methylene chloride layer is washed with aqueous base, then water, and ethanol is added to precipitate the diamine product.

2-Chloro-4'-(N-succinimido)benzophenone is prepared as follows: To a solution of 2-chloro-4'-fluoro-benzophenone (100 mmol) in NMP (100 ml) is added succinimide (110 mmol) and potassium carbonate (200 mmol). After heating at 80° C. for 8 hours, 100 ml of water is added and the mixture extracted with methylene chloride. The product is recrystallized from methylene chloride - ethanol.

EXAMPLE 33

Preparation of a macromonomer of the structure (1) where $G_1$ is benzoyl, $G_2$ through $G_4$ are hydrogen, E is 3-aminophenyl, and $DP_n=16$.

General Procedure I is followed, where the monomer is 2,5-dichlorobenzophenone (11.5 mmol), and the endcapper is N-(3-chlorophenyl)succinimide (1.15 mmol) (prepared from 3-chloroaniline using General Procedure IV). The resulting macromonomer is in the protected succinimide form. The free amine is obtained by refluxing the succinimide with 25 ml of 10% HCl in ethanol for six hours, followed by neutralization with sodium hydroxide, and extraction into methylene chloride. The methylene chloride layer is washed with aqueous base, then water, and ethanol is added to precipitate the diamine product.

EXAMPLE 34

Preparation of a macromonomer of the structure (1) where $G_1$ is benzoyl, $G_2$ through $G_4$ are hydrogen, E is 4-(2-aminoethyl)phenyl, and $DP_n=16$.

General Procedure I is followed, where the monomer is 2,5-dichlorobenzophenone (11.5 mmol), and the endcapper is N-2-(4-chlorophenyl)ethylsuccinimide (1.15 mmol) (prepared from 2-(4-chlorophenyl) ethylamine using General Procedure IV). Deprotection, as in the general procedure, yields the amino-functionalized macromonomer.

EXAMPLE 35

Preparation of a macromonomer of the structure (1) where $G_1$ is benzoyl, $G_2$ through $G_4$ are hydrogen, E is 7-amino-2-fluorenyl, and $DP_n=14$.

The procedure of Example 32 is followed, where the endcapper is 2-bromo-7-N-succinimidofluorene (1.533 mmol) (prepared from 2-amino-7-bromofluorene using General Procedure IV). Deprotection yields the amino-functionalized macromonomer.

EXAMPLE 36

Preparation of a macromonomer of the structure (1) where $G_1$ is benzoyl, $G_2$ through $G_4$ are hydrogen, E is 4-(2-methoxy-5-methylaniline), and $DP_n=19$.

The procedure of Example 32 is followed, where the endcapper is the phthalimide of 4-chloro-2-meth-oxy-5-methylaniline (0.92 mmol). Deprotection yields a macromonomer having structure 1 where $G_1$ is benzoyl, $G_2$ through $G_4$ are hydrogen, E is 4-(2-methoxy-5-methylaniline), and $DP_n=19$.

EXAMPLE 37

Preparation of a macromonomer of the structure (1) where $G_1$ is benzoyl, $G_2$ through $G_4$ are hydrogen, E is 4-phenol, and $DP_n=14$.

The procedure of Example 32 is followed, where the endcapper is 4-chlorophenylacetate (1.533 mmol). Deprotection yields the hydroxy-functionalized macromonomer.

4-Chlorophenyl acetate is prepared by acylation of 4-chlorophenol with acetic anhydride using Schotten Baumann conditions.

EXAMPLE 38

Preparation of a macromonomer of the structure 1 where $G_1$ is benzoyl, $G_2$ through $G_4$ are hydrogen, E is 4-(4'-hydroxybenzophenone), and $DP_n=10$.

The procedure of Example 32 is followed, where the endcapper is 4-acetoxy-4'-chlorobenzophenone (2.3 mmol), prepared by acylation of 4-chloro-4'-hydroxybenzophenone with acetic anhydride using Schotten Baumann conditions.

EXAMPLE 39

Preparation of a macromonomer of the structure (1) where $G_1$ is benzoyl, $G_2$ through $G_4$ are hydrogen, E is 4-phenethylalcohol, and $DP_n=16$.

The procedure of Example 32 is followed, where the endcapper is the tetrahydropyranyl ether of 4-chlorophenethyl alcohol (1.15 mmol). Deprotection yields the hydroxy-functionalized macromonomer.

EXAMPLE 40

Preparation of a macromonomer of the structure (1) where $G_1$ is carbonylmorpholine, $G_2$ through $G_4$ are hydrogen, E is 3-aminophenyl, and $DP_n=16$.

General Procedure I is followed, where the monomer is N-(2,5-dichlorobenzoyl)morpholine (11.5 mmol), and the endcapper is N-(3-chlorophenyl)succinimide (1.15 mmol). Deprotection yields the amino-functionalized macromonomer.

EXAMPLE 41

Preparation of a macromonomer of the structure (1) where $G_1$ is carbonylmorpholine, $G_2$ through $G_4$ are hydrogen, E is 4-(2-aminoethyl)phenyl, and $DP_n=16$.

General Procedure I is followed, where the monomer is N-(2,5-dichlorobenzoyl)morpholine (11.5 mmol), and the endcapper is N-2(4-chlorophenyl)ethylsuccinimide (1.15 mmol). Deprotection yields the amino-functionalized macromonomer.

EXAMPLE 42

Preparation of a macromonomer of the structure (1) where $G_1$ is carbonylmorpholine, $G_2$ through $G_4$ are hydrogen, E is 7-amino-2-fluorenyl, and $DP_n=14$.

General Procedure I is followed, where the monomer is N-(2,5-dichlorobenzoyl)morpholine (11.5 mmol), and the endcapper is 2-bromo-7-N-succinimidofluorene (1.533 mmol). Deprotection yields the amino-functionalized macromonomer.

EXAMPLE 43

Preparation of a macromonomer of the structure 1 where $G_1$ is carbonylmorpholine, $G_2$ through $G_4$ are hydrogen, E is 4-(4'-hydroxybenzophenone), and $DP_n=16$.

General Procedure I is followed, where the monomer is N-(2,5-dichlorobenzoyl)morpholine (11.5 mmol), and the endcapper is 4-acetoxy-4' chlorobenzophenone (1.15 mmol). Deprotection yields the hydroxy-functionalized macromonomer.

EXAMPLE 44

Preparation of a macromonomer of the structure 1 where $G_1$ and $G_3$ are phenyl, $G_2$ through $G_4$ are hydrogen, E is 4-amino-5-methoxy-2-methylphenyl, and $DP_n=19$.

General Procedure I is followed, where the monomer is 1,4-diiodo-2,5-diphenylbenzene (11.5 mmol), and the endcapper is 4-chloro-2-methoxy-5-methylphenylphthalimide (0.92 mmol). Deprotection yields the amino-functionalized macromonomer.

1,4-Diiodo-2,5-diphenylbenzene is prepared as described in M. Hart and K. Harada, *Tetrahedron Letters,* Vol. 26, No. 1, pages 29–32 (1985).

EXAMPLES 45–47: BISMALEIMIDE RIGID-ROD MACROMONOMERS

EXAMPLE 45

Preparation of a macromonomer of the structure (1) where $G_1$ is benzoyl, $G_2$ through $G_4$ are hydrogen, E is 4-maleimidophenyl and $DP_n=10$.

General Procedure I is followed, where the monomer is 2,5-dichlorobenzophenone (11.5 mmol), and 2.30 mmol of the endcapper 4-chloro-(N-succinimido)benzene (prepared from 4-chloroaniline using General Procedure IV) is employed. The free amine obtained upon deprotection as described in the general procedure has n=10.

The amine-terminated rigid-rod macromonomer is dissolved in 25 ml of N,N-dimethylacetamide. To this solution, 2.5 mmol of maleic anhydride and 0.25 mols of p-toluenesulfonic acid are added. The solution is refluxed for 12 hours and then cooled to room temperature. The solution is poured into toluene, whereupon the product precipitates. The product is filtered, washed with toluene, and dried to constant weight.

EXAMPLE 46

Preparation of a macromonomer of the structure (1) where $G_1$ is 4-phenoxybenzoyl, $G_2$ through $G_4$ are hydrogen, E is 4-(4-maleimidophenoxy)phenyl and $DP_n=10$.

General Procedure I is followed, where the monomer is 2,5-dichloro-4'-phenoxybenzophenone (11.5 mmol). 2.30 mmol of the endcapper 4-chloro-4'-(N-succinimido) diphenyl ether is employed. The free amine obtained upon deprotection has n=10.

The amine-terminated rigid-rod macromonomer is dissolved in 25 ml of toluene. To this solution, 2.5 mmol of maleic anhydride and 0.25 mmol p-toluenesulfonic acid are added. The solution is refluxed for 12 hours and then cooled to room temperature. The solvent is evaporated, and the product is washed repeatedly with 1M potassium carbonate, followed by washing with water. The bismaleimide macromonomer is then dried to constant weight.

The endcapper 4-chloro-4'-(N-succinimido) diphenylether is prepared by an Ullmann ether synthesis. The reaction of 4-chlorophenol with 4-bromonitrobenzene yields 4-chloro-4'-(nitro)diphenylether. Reduction of the nitro group under standard conditions yields the corresponding aminochloro derivative. The succinimide is prepared by allowing succinic anhydride to react with the aminochloro compound in toluene, using p-toluenesulfonic acid as catalyst.

EXAMPLE 47

Preparation of a macromonomer of the structure 1 where $G_1$ and $G_3$ are butoxy, $G_2$ and $G_4$ are H, E is 5-(2-maleimido)benzophenone, and $DP_n=20$.

General Procedure I is followed, using 1,4-di-chloro-2,5-dibutoxybenzene (11.5 mmol) as monomer and 1.15 mmol of the succinimide derived from 2-amino-5-chlorobenzophenone as endcapper. The free amine is obtained upon deprotection as described in General Procedure V.

The monomer 1,4-dichloro-2,5-dibutoxybenzene can be obtained by treatment of 2,5-dichlorohydroquinone (R. L. Beddoes, J. M. Bruce, H. Finch, L. M. J. Heelam, I. D. Hunt, and O. S. Mills, J. C. S. Perkin I, 2670, (1981).) with sodium carbonate in N,N'-dimethylacetamide, followed by addition of approximately 2.2 equivalents of n-butanol.

The amine-terminated rigid-rod macromonomer is dissolved in 25 ml of toluene. To this solution 1.25 mmol of maleic anhydride and 0.13 mmol p-toluenesulfonic acid are added. The solution is refluxed for 12 hours and then cooled to room temperature. The solvent is evaporated, and the product is washed repeatedly with 1M potassium carbonate, followed by washing with water. The product is then dried to constant weight.

EXAMPLES 48–51: NADIMIDE RIGID-ROD MACROMONOMERS

EXAMPLE 48

Preparation of a macromonomer of the structure (1) where $G_1$, is benzoyl, $G_2$ through G4 are hydrogen, E is 2-(nadimido benzene), and $DP_n=16$.

The amine-terminated rigid-rod macromonomer of Example 33 is dissolved in 25 milliliters of N,N-di-methylacetamide. To this solution, 2.5 mmol of cis-5-norbornene-endo-2,3-dicarboxylic anhydride and 0.25 mmol p-toluenesulfonic acid are added. The solution is refluxed for 12 hours and then cooled to room temperature. The solution is poured into toluene, whereupon the product precipitates. The product is filtered, washed with toluene, and dried to constant weight to give the nadimide terminated macromonomer.

EXAMPLE 49

Preparation of a macromonomer of the structure (1) where $G_1$ is 4-phenoxybenzoyl, $G_2$ through $G_4$ are H, E is 2-(4'-nadimidobenzophenone), and $DP_n=10$.

General Procedure I is followed, where the monomer is 4'-phenoxy-2,5-dichlorobenzophenone (11.5 mmol), and 2.30 mmol of the endcapper 2-chloro-4'-(N-succini-mido) benzophenone is employed. The free amine obtained upon deprotection has n=10.

The amine-terminated rigid-rod macromonomer is dissolved in 25 ml of N,N-dimethylacetamide. To this solution, 2.5 mmol of cis-5-norbornene-endo-2,3-di-carboxylic and 0.25 mols of p-toluenesulfonic acid are added. The solution is refluxed for 12 hours and then cooled to room temperature. The solution is poured into toluene, whereupon the product precipitates. The product is filtered, washed with toluene, and dried to constant weight.

EXAMPLE 50

Preparation of a macromonomer of the structure (1) where $G_1$ and $G_3$ are butoxy, $G_2$ and $G_4$ are H, E is 5-(2-nadimido)benzophenone, and $DP_n=20$.

The amine-terminated rigid-rod macromonomer of Example 47 is dissolved in 25 ml of N,N-dimethylacetamide. To this solution, 1.13 mmol cis-5-norbor-nene-endo-2, 3-dicarboxylic anhydride and 0.13 mmol p-toluenesulfonic acid are added. The solution is refluxed for 12 hours and then cooled to room temperature. The solution is poured into toluene, whereupon the product precipitates. The product is filtered, washed with toluene, and dried to constant weight.

EXAMPLE 51

Preparation of a macromonomer of the structure (1) where $G_1$ is 4-phenoxybenzoyl, $G_2$ through $G_4$ are H, E is 2-(4'-nadimido)benzophenone, and $DP_n=20$.

General Procedure I is followed, where the monomer is 2,5-dichloro-4'-phenoxybenzophenone (11.5 mmol) and 1.15 mmol of the endcapper 2-chloro-4'-(N-succini-mido) benzophenone is employed. The free amine obtained upon deprotection as described in Example 1 has n=20.

The amine-terminated rigid-rod macromonomer is dissolved in 25 ml of N,N-dimethylacetamide. To this solution, 1.13 mmol cis-5-norbornene-endo-2,3-di-carboxylic anhydride and 0.13 mmol p-toluenesulfonic acid are added. The solution is refluxed for 12 hours and then cooled to room temperature. The solution is poured into toluene, whereupon the product precipitates. The product is filtered, washed with toluene, and dried to constant weight.

EXAMPLES 52–55: BENZOCYCLOBUTENE RIGID-ROD MACROMONOMERS

EXAMPLE 52

Preparation of a macromonomer of the structure (1) where $G_1$ is carbophenoxy (-(CO)OC$_6$H$_5$) $G_2$ through $G_4$ are H, E is 4-benzocyclobutene, and $DP_n$=10.

General Procedure I is followed, where the monomer is 2,5-dichlorophenylbenzoate (11.5 mmol) (prepared by benzoylation of 2,5-dichlorophenol with benzoyl chloride using Schotten Baumann conditions) and 2.3 mmol of the endcapper 4-chlorobenzocyclobutene is employed. The endcapper 4-chlorobenzocyclobutene is obtained from the commercially available monosodium salt of 4-chlorophthalic acid. Reduction to the dibenzyl alcohol using lithium aluminum hydride in refluxing tetrahydrofuran, followed by treatment with phosphorous tribromide in refluxing toluene, yields the dibenzyl obromide. Treatment of this compound with disodium sulfide in refluxing 95% ethanol yields 4-chloro-benzotetrahydrothiophene. This compound is treated with peracetic acid to yield the corresponding sulfone. Pyrolysis of this sulfone in vacuo yields 4-chlorobenzocyclobutene [reference to synthesis: M. P. Cava and A. A. Deana, JACS 81, 4266 (1959)].

EXAMPLE 53

Preparation of a macromonomer of the structure (1) where $G_1$ and $G_2$ form a bridging group -CHCHCHN-, $G_3$ and $G_4$ are H, E is 4-benzocyclobutene, and $DP_n$=10.

General Procedure I is followed, where the monomer is 5,8-dichloroquinoline (11.5 mmol) [reference to synthesis: M. Gordon and D. E. Pearson, J. Org. Chem., 29, 329 (1964)], and 2.3 mmol of the endcapper 4-chlorobenzocyclobutene is employed.

EXAMPLE 54

Preparation of a macromonomer of the structure 2 where $A_1$ and $A_2$ are N, $G_1$ and $G_2$ are nil, $G_3$ and $G_4$ are H, E is 4-benzocyclobutene, and $DP_n$=6.

General Procedure I is followed, where the monomer is commercially available 3,6-dichloropyridazine (11.5 mmol), and 3.8 mmol of the endcapper 4-chlorobenzo-cyclobutene is employed.

EXAMPLE 55

Preparation of a macromonomer of the structure (1) where $G_1$ is carbonylpiperidine, $G_2$ through $G_4$ are H, E is 4-benzocyclobutenemethane, and $DP_n$=20.

General Procedure I is followed, where the monomer is N-(2,5-dichlorobenzoyl)piperidine (11.5 mmol) and 1.15 mmol of the endcapper 4-iodomethylbenzocyclobutene is employed.

The endcapper 4-iodomethylbenzocyclobutene can be obtained by first esterifying commercially available 3,3-dimethylbenzoic acid with ethanol, using HCl as a catalyst. The corresponding ethyl ester derivative is treated with N-bromosuccinimide to yield the dibenzyl bromide. Treatment of this compound with disodium sulfide in refluxing 95% ethanol yields ethylbenzo-tetrahydro-thiophene-4-carboxylate. This compound is treated with peracetic acid to yield the corresponding sulfone. Pyrolysis of this sulfone in vacuo leads to ethylbenzocyclobutene-4-carboxylate [ref. M. P. Cava and A. A. Deana, JACS 81, 4266 (1959)]. This ethyl ester is reduced to the corresponding benzyl alcohol with lithium aluminum hydride in THF. The benzyl alcohol is treated with p-toluenesulfonyl chloride in pyridine at room temperature to form the corresponding sulfonate ester. This compound, when treated with sodium iodide in acetone, yields 4-iodomethylbenzocyclobutene.

EXAMPLES 56–58: BIPHENYLENE-TERMINATED MACROMONOMERS

EXAMPLE 56

Preparation of a macromonomer of the structure (1) where $G_1$ is carbonylmorpholine, $G_2$ through $G_4$ are H, E is 2-biphenylene and $DP_n$=10.

General Procedure I is followed, where the monomer is N-(2,5-dichlorobenzoyl)morpholine (11.5 mmol), and 2.30 mmol of the endcapper 2-chloro-biphenylene is employed.

The endcapper 2-chlorobiphenylene is prepared from the corresponding 2-aminobiphenylene [Reference to synthesis: W. Vancraeynest and J. K. Stille, Macromolecules, 13, 1361 (1980)]. The amine is first converted to 2-diazobiphenylene by treatment with nitrous acid, followed by addition of cuprous chloride, which results in formation of 2-chlorobiphenylene (Sandmeyer reaction).

EXAMPLE 57

Preparation of a macromonomer of the structure (1) where $G_1$ is phenyl, $G_1$ through $G_4$ are H, E is 2-bipheny-lene, and $DP_n$=20.

General Procedure I is followed, where the monomer is 2,5-dichlorobiphenyl (11.5 mmol). 1.15 mmol of the endcapper 2-chlorobiphenylene is employed, yielding a biphenylene-terminated rigid-rod macromonomer.

The monomer 2,5-dichlorobiphenyl is prepared by treating dichlorobenzene with 75% dibenzoyl peroxide (25% water) for 2.5 hours from 100° C. to 140° C. The product is isolated by distillation under reduced pressure [H. T. Land, W. Hatke, A. Greiner, H. W. Schmidt, W. Heitz, Makromol. Chem., 191, 2005 (1990)].

EXAMPLE 58

Preparation of a macromonomer of the structure (1) where $G_1$ is phenyl, $G_1$ through $G_4$ are H, E is 2-bipheny-lene, and $DP_n$=20.

General Procedure I is followed, as in Example 29; 1.15 mmol of the endcapper 2-chlorobiphenylene is employed, and the resulting biphenylene terminated rigid-rod macromonomer has structure 1 where $G_1$ is benzoyl, the remaining G's are H, E is 2-biphenylene and n=20.

EXAMPLE 59: ACETYLENE TERMINATED MACROMONOMERS

EXAMPLE 59

Preparation of a macromonomer of the structure (1) where $G_1$ is benzoyl, $G_2$ through $G_4$ are H, E is ethynyl, and $DP_n$=10.

To the monomer of Example 11 (4.2 g, 1 mmol) in 25 ml of anisole (cooled to 0° C.) is added lithium diisopropylamine (LDA) (2 mmol) and diethyl chlorophosphate (2 mmol). The reaction mixture is warmed to room temperature and additional LDA (2.2 mmol) is added. After 4 hours, the mixture is poured into 100 ml of ethanol and the precipitate is filtered, washed with 25 ml of ethanol, and dried.

EXAMPLES 60–62: EPOXIDE-TERMINATED MACROMONOMERS

EXAMPLE 60

Preparation of a macromonomer of the structure (1) where $G_1$ is carbonylmorpholine, $G_2$ through $G_4$ are H, E is 4-styrene oxide, and $DP_n$ is 15.

General Procedure I is followed, where the monomer is N-(2,5-dichlorobenzoyl)morpholine (11.5 mmol), and 1.53 mmol of the endcapper 4-chlorobenzaldehyde is employed. Upon isolation of the aldehyde-terminated rigid-rod macromonomer, conversion to the styrene oxide-terminated [e.g., bis(epoxide)] macromonomer is carried out by treating the bis(aldehyde) with dimethylsulfonium methylide. This is accomplished by first preparing the anion of dimethyl sulfoxide (DMSO) by treatment with 1.68 mmols of sodium hydride at 80° C. At room temperature, this solution is diluted with tetrahydrofuran, cooled to 5° C., and 1.68 mmols of trimethylsulfonium iodide added to form dimethylsulfonium methylide. This solution is then added by syringe to a solution of the bis(aldehyde) macromonomer dissolved in methylene chloride [E. J. Corey and M. Chaykovsky, *Journal of the American Chemical Society*, 87, 1345 (1965); also Ibid, page 1353.]

The product bis(epoxide) rigid-rod macromonomer is isolated by precipitation into water. Soxhlet extraction of the product with a 90:10 mixture of water/triethylamine for 24 hours yields the purified bis(epoxide).

EXAMPLE 61

Preparation of a macromonomer of the structure (1) where $G_1$ is benzoyl, $G_2$ through $G_4$ are H, E is 4-(1,2-epoxyethylphenoxy)phenyl and $DP_n$ is 10.

General Procedure I is followed, where the monomer is 2,5-dichlorobenzophenone (11.5 mmol). 2.3 mmol of the endcapper 3-(4-chlorophenoxy)-benzaldehyde is employed. Upon isolation of the aldehyde-terminated rigid-rod macromonomer, conversion to the bis(epoxide) macromonomer is carried out by treating the bisialdehyde) with dimethylsulfonium methylide, as described in the preceding example.

EXAMPLE 62

Preparation of a macromonomer of the structure (1) where $G_1$ and $G_3$ are methyl, $G_2$ and $G_4$ are H, E is 4-N,N-bis(2,3-epoxypropyl)aminophenyl, and $DP_n=6$.

General Procedure I is followed, where the monomer is 2,5-dichloro-p-xylene (11.5 mmol) and 3.8 mmol of the endcapper 4-(N-succinimido)chlorobenzene is employed. The free amine obtained upon deprotection as described in General Procedure V has n=6.

The amine-terminated rigid-rod macromonomer is suspended in 25 ml of dichloromethane (or, alternatively, triethylamine), and 4.0 mmols of epichlorohydrin is added. The solution is allowed to stir for two hours at room temperature, at which time the bis(epoxide) rigid-rod macromonomer is isolated by pouring into a solution of water/triethylamine in a 90:10 ratio. The precipitated macromonomer is further purified by Soxhlet extraction with a 90:10 water/triethylamine solution for 24 hours.

EXAMPLE 63

Preparation of a macromonomer of the structure (1) where $G_1$ is benzoyl, $G_2$ through $G_4$ are hydrogen, E is 5-veratryl, and $DP_n=25$.

Anhydrous nickel(II) chloride (50 mg, 0.39 mmol), triphenylphosphine (750 mg, 2.86 mmol), sodium iodide (150 mg, 1.0 mmol), and 325 mesh activated zinc powder (1.2 g, 18 mmol) are placed into a 25 ml flask under an inert atmosphere along with 5 ml of anhydrous N-methylpyrrolidinone (NMP). This mixture is stirred at 50° C. for about 10 minutes, leading to a deep-red coloration. A solution of 11.5 mmol of monomer in 10 ml of anhydrous NMP is then added by syringe. After stirring for 10 hours, 0.92 mmol 5-bromoveratraldehyde is added to the resulting viscous solution, which is stirred for an additional 10 hours. The solution is then poured into 100 ml of 1 molar hydrochloric acid in ethanol to dissolve the excess zinc metal and to precipitate the macromonomer. This suspension is filtered and the precipitate triturated with acetone, and dried to afford a light tan to white powder, in nearly 100% yield. The aldehyde function of the veratryl end groups may then be reduced to a hydroxymethyl group. Alternatively the aldehyde group may be converted into an aminomethyl group by forming the Schiff's base with ammonia or a primary or secondary amine, followed by reduction.

EXAMPLE 64

Preparation of a macromonomer of the structure (1) where $G_1$ is benzoyl, $G_2$ through $G_4$ hydrogen, E is $-NH_2$, and $DP_n=50$.

Anhydrous nickel(II) chloride (0.4 mmol), triphenylphosphine (750 mg, 2.86 mmol), sodium iodide (150 mg, 1.0 mmol), and 325 mesh activated zinc powder (1.2g, 18 mmol) are placed into a 25 ml flask under an inert atmosphere along with 5 ml of anhydrous N-methylpyrrolidinone (NMP). This mixture is stirred at 50° C. for about 10 minutes, leading to a deep-red coloration. A solution of 10 mmol of monomer in 10 ml of anhydrous NMP is then added by syringe. After stirring for 10 hours, the reaction is quenched with 10 mmol sodamide in 1 ml NMP and stirred for an additional hour. The solution is then poured into 100 ml of 1 molar hydrochloric acid in ethanol to dissolve the excess zinc metal and precipitate the macromonomer. This suspension is filtered and the precipitate triturated with acetone, and dried to afford a light tan to white powder, in nearly 100% yield.

EXAMPLE 65

Preparation of a macromonomer of the structure (1), where $G_1$ is benzoyl, $G_2$ through $G_4$ are hydrogen, E is carboxy, and $DP_n=20-25$.

Anhydrous nickel(II) chloride (50 mg, 0.39 mmol), triphenylphosphine (750 mg, 2.86 mmol), sodium iodide (175 mg, 1.17 mmol), and 325 mesh activated zinc powder (0.5–1.0 g, 7.5–15 mmol) are placed into a 25 ml flask under an inert atmosphere along with 7 ml of anhydrous N-methylpyrrolidinone (NMP). This mixture is stirred at 50° C. for about 10–20 minutes, leading to a deep-red coloration. A solution of 2,5-dichlorobenzophenone (1.1 g, 4.38 mmol) in 8 ml of anhydrous NMP is then added all at once by syringe. After a period of about 20 minutes, the reaction is pressurized with carbon dioxide. After stirring for about 24 hours, the resulting viscous solution is poured into 100 ml of 1 molar hydrochloric acid in ethanol to hydrolyze the metal carboxylate derivative, dissolve the excess zinc metal and precipitate the macromonomer. This suspension is filtered and the precipitate triturated with acetone and dried to afford the carboxy-terminated macromonomer.

EXAMPLE 66

Preparation of a macromonomer of the structure (1) where $G_1$ is OH, $G_2$ through $G_4$ are hydrogen, E is 3-benzaldehyde, and $DP_n=40$.

The Grignard reagent of 2,5-dibromophenol-tetra-hydropyranylether, is prepared by addition of 2,5-dibromophenol-tetrahydropyranylether (50 mmol) to magnesium turnings, 50 mmol, in dry tetrahydrofuran (THF). Upon completion of the reaction, 2.5 mmol 2-(3-bromophenyl)-1,3-dioxolane is added, followed by 0.1 mmol of bis(triphenylphosphine)nickel(II) chloride. The solution is heated to reflux for 6 hr. The polymer is precipitated by addition of the cooled solution to dilute acid.

EXAMPLE 67

Preparation of a macromonomer of the structure (1) where $G_1$ and $G_3$ are phenyl, $G_2$ through $G_4$ are hydrogen, E is 4-aminophenyl, and $DP_n=5$.

A mixture of 4-bromo-2,5-diphenylbenzeneboronic acid (10 mmol), 4-amino-benzeneboronic acid (2 mmol), tetrakis (triphenylphosphine) palladium (0.1 mmol), benzene (50 ml) and aqueous $Na_2CO_3$ (2M, 40 ml) are refluxed and stirred under $N_2$ for 48 hours. The mixture is then poured into acetone (250 ml) to precipitate the macromonomer.

4-Bromo-2,5-diphenylbenzeneboronic acid is prepared as follows: A solution of n-butyllithium (1.6 M, 15 ml) in hexane is added slowly to a cooled (–40° C.) solution of 1,4-di-bromo-2,5-diphenylbenzene (25 mmol) in diethyl-ether (100 ml). This mixture is allowed to warm to room temperature and is stirred for 2 hours. This solution is transferred into a dropping funnel and added to a cooled (–60° C.) solution of trimethylborate (74 mmol) in ether (200 ml). It is then stirred for 8 hours at room temperature. After hydrolysis with aqueous HCl (2M, 150 ml), the layers are separated and the aqueous layer is extracted with ether (100 ml). The solvent is then removed from the combined organic layers and water (5 ml) and petroleum ether (100) are added. The precipitate is recovered by filtration, and recrystallized from toluene.

EXAMPLES 68–82: POLYMERS INCORPORATING RIGID-ROD MACROMONOMERS

EXAMPLE 68

A solution of the macromonomer of Example 39 (1 mmol, 2.76 g), hexamethylenediamine (99 mmol, 11.505 g), and pyridine (20 ml) in 150 ml NMP is added to a solution of terepthaloyl chloride (100 mmol, 20.302 g) in 50 ml NMP. The solution is warmed to 50° C. for 4 hours, then poured into water to precipitate the copolymer. The resulting polyhexamethyleneadipamide-co-poly-2,5-benzo-phenone is approximately 10% by weight rigid-rod.

EXAMPLE 69

The procedure for preparation of bisphenol-A polycarbonate given in *Macromolecular Synthesis*, J. A. Moore, Ed., John Wiley & Sons; New York; 1977, Collective Vol. 1, pp 9–12 (incorporated herein by this reference); is followed, except that 2 g of the macromonomer of Example 38 is added along with the bisphenol-A. More specifically, a 500 ml four-necked flask (or resin pot) equipped with a stirrer, thermometer, a wide bore gas inlet tube, and a gas outlet is charged with 22.8 g (0.10 mol) of bisphenol-A, 2 g of the macromonomer of Example 38, and 228 ml of pyridine. Phosgene at a rate of 0.25 g/min. is passed into the rapidly stirred reaction mixture, which is maintained at 25°–30° C. with a water bath. Pyridine hydrochloride will begin to separate from the reaction mixture after about 25 minutes. This is an indication that the reaction is about 60 percent completed. Approximately 15 minutes later, a marked increase in viscosity will be noted over a period of 2–3 minutes; the polymerization is then essentially completed. The copolymer may be precipitated directly in the reaction flask and is approximately 9 percent by weight rigid-rod.

EXAMPLE 70

The procedure for preparation of phenol-formaldehyde resin given in *Macromolecular Synthesis*, J. A. Moore, Ed., John Wiley & Sons; New York; 1977, Collective Vol. 1, pp 211–213 (incorporated herein by this reference), is followed, except that 893 g of phenol is used, and 30 g of the macromonomer of Example 38 is added along with the phenol. More specifically, a 3 L three-necked round bottom flask (or resin pot) equipped with a Teflon or stainless steel paddle-type stirrer, thermometer, efficient bulb-type reflux condenser, and heating mantle is charged with 893 g (9.5 mol) of phenol (99 percent purity), 70 g (0.75 mol) of aniline, 30 g (0.0163 mol) of the macromonomer of Example 38, 1,130 g of 37.2 percent formaldehyde solution (14 mols) and 110 g of a 28.5 percent hot water solution of barium hydroxide octahydrate. The pressure is reduced to 300–350 torr and the reactants are heated slowly to a reflux temperature of 80° C. and maintained there for 15 min. The reflux condenser is then replaced with a condenser set for distillation, and the resin is dehydrated at 10–20 torr to a final temperature of 80°–90° C. As the dehydration proceeds, the molecular weight and viscosity of the condensate increase progressively, and the resin becomes increasingly sensitive to further heating. When the "gel time," as determined by the so-called stroke cure test, falls to 65–85 sec., the apparatus is quickly disassembled and the resin is poured in a thin layer into a large shallow vessel covered with heavy aluminum foil to provide rapid cooling. The resulting resin is approximately 5% by weight rigid-rod.

EXAMPLE 71

The procedure for preparation of polyethylene terephthalate given in *Macromolecular Synthesis*, J. A. Moore, Ed., John Wiley & Sons; New York; 1977, Collective Vol. 1, pp 17–21 (incorporated herein by this reference), is followed, except that 3 g of the macromonomer of Example 5 is added to the charge along with the ethylene glycol. More specifically, a glass "polymer tube" about 25 mm by 250 mm, sealed to a 10 mm by 70 mm neck carrying a side arm for distillation is charged with 13.6 g (0.07 mol) of dimethyl terephthalate (DMT), 3 g of the macromonomer of Examiner 5, 10 g (8.8 ml, 0.16 mol) of ethylene glycol, 0.022 g (0.15% based on DMT) of calcium acetate dihydrate, and 0.005 g (0.035% based on DMT) of antimony trioxide. The charge is melted by submerging the tube about half way in the vapors of boiling ethylene glycol (197° C.), and a fine capillary connected to nitrogen under pressure, is introduced through the neck of the tube. A vacuum tight seal is made with a piece of heavy walled rubber tubing, well lubricated with silicone grease. The capillary must be adjusted to reach the very bottom of the polymer tube. Methyl alcohol distills rapidly for a few minutes. After one hour, the tube is adjusted to be heated as completely as possible by the glycol vapors, and heating at 197° C. is continued for two hours more. The polymer tube is then transferred to a 222° C. (methyl salicylate) vapor bath for 15 minutes, during which time excess glycol distills and polymerization begins.

The side arm of the polymer tube is then connected by means of a short piece of heavy walled tubing to a receiver having a side arm for collection under vacuum. The tube is heated at 283° C. (dimethyl phthalate). Polymerization proceeds and glycol distills slowly. After 5 to 10 minutes vacuum is applied very cautiously and the pressure is brought to 0.2 torr or less in about 15 minutes. Polymerization should be complete within 3 hours. The tube is then filled with nitrogen, removed from the vapor bath and allowed to cool. The glass is cracked away from the mass of polymer by wrapping it in a towel and tapping with hammer. The last of the glass, which adheres very tenaciously, must be removed with a coarse file.

The resulting copolymer is approximately 15% by weight rigid-rod.

EXAMPLE 72

The procedure of Padaki, Norris, and Stille for the preparation of poly [2,2'-(p,p'-oxydipheny-lene)-6, 6'-oxy-bis(4-phenylquinoline)], given in *Macromolecular Synthesis;* J. A. Moore, Ed., John Wiley & Sons; New York; 1985, Vol. 9, pp. 53–55 (incorporated herein by this reference), is followed, except that 0.2797 g of 4,4'-diacetyldiphenyl ether is used along with 0.7500 g of the diacetyl-substituted macromonomer of Example 11 (with molecular weight of about 4200). More specifically, a mixture of 0.5223 g (1.279 mmol) of 4,4'-diamino-3, 3'-dibenzoyldiphenyl ether, 0.2797 g (1.100 mmol) of 4,4'-diacetyldiphenyl ether, 0.7500 g (0.179 mmol) of the diacetyl-substituted macromonomer of Example 11 (with molecular weight of about 4200), 8.8 g (32 mmol) of di-m-cresyl phosphate, and 1.5 g (14 mmol) of distilled m-cresol is stirred in a three-neck polymerization flask equipped with a nitrogen inlet, an overhead stirrer and a nitrogen outlet. The reaction mixture is flushed with nitrogen for about 5 minutes and then heated in an oil bath from room temperature to 135° C. to 140° C. in about 30 minutes. It is maintained at this temperature for 48 hours under a static nitrogen atmosphere. The resulting clear, highly viscous solution is poured slowly into a stirred solution of 500 ml of ethanol containing 50 ml of triethylamine to yield an off-white fibrous material. This fibrous polymer is suspended in a small amount (about 50 ml) of ethanol containing 10% v/v of triethylamine, chopped in a blender and collected by filtration. The polymer is continuously extracted for 24 hours in a Soxhlet apparatus with ethanol containing 10% v/v triethylamine. It is then air dried and then further dried at 110° C. and 0.1 torr for 4 hours. The polymer is redissolved in 30 ml of chloroform and reprecipitated by slow addition to a stirred solution of 300 ml of ethanol containing 30 ml of triethylamine. The precipitated fibrous polymer is suspended in about 50 ml of ethanol containing 5 ml of triethylamine, chopped in a blender, collected by filtration, air dried, and then dried further at 110° C. and 0.1 torr for 24 hours to yield the copolymer, which is approximately 50% by weight rigid rod.

EXAMPLE 73

The procedure of Wynn, Glickman, and Chiddix for the preparation of 4-nylon, given in *Macromolecular Synthesis;* J. A. Moore, Ed., John Wiley & Sons; New York; 1977, Coll. Vol. 1, pp. 321–323 (incorporated herein by this reference), is followed, except that 10 g of the ester-substituted macromonomer of Example 4 is added just prior to the addition of silicon tetrachloride. More specifically, a 250 ml 3-necked round bottom flask equipped with stirrer, thermometer and Claisen head suitable for vacuum distillation is charged with a 120 g of freshly distilled 2-pyrrolidone. The charge is heated under nitrogen to 80° C. with a Glas-Col mantel. Flake potassium hydroxide (97%) (3.4 g) is added. The water formed, together with about 20 ml of monomer, is rapidly distilled from the flask at 1 torr. The hot solution is rapidly transferred to an 8 oz. polyethylene bottle previously purged with nitrogen. Ten g of the ester-substituted macromonomer of Example 4 is then added followed by 0.5 g of silicon tetrachloride. The bottle is capped, agitated by hand, and allowed to cool to room temperature. After 10 minutes and at a temperature of about 50° C., polymerization is indicated by precipitation of solid polymer. After 24 hours at room temperature, the mixture is very hard. It is broken with a hammer and the bottle is cut open for its removal. The lumps are then blended with a 150 ml of water containing 0.1% formic acid in a blender. The powdered product is filtered and washed in the filter with 150 ml of 0.1% formic acid followed by three 100 ml washings with distilled water. It is finally washed with alcohol and dried at 3 torr at 70° C. The resulting resin is approximately 10–15% by weight rigid-rod.

EXAMPLE 74

The procedure of Conciatori and Chenevey for the preparation of poly [2,2'-(m-phenylene)-5,5'-bibenzimidazole], given in *Macromolecular Synthesis;* J. A. Moore, Ed., John Wiley & Sons; New York; 1977, Coll. Vol. 1, pp. 235–239 (incorporated herein by this reference), is followed, except that 38.836 g of DPIP is used along with 15.06 g of the ester-substituted macromonomer of Example 31 (with molecular weight of about 5020). More specifically, a two-stage polymerization is carried out. For the first stage, a 1 liter, 3 necked flask is charged with 26.784 g (0.125 mol) of purified 3,3'-diaminobenzidine (DAB), 38.836 g (122 mmol) of diphenyl isophthalate (DPIP), and 15.06 g (3 mmol) of the ester-substituted macromonomer of Example 31 (with molecular weight of about 5,020). The flask is immersed in an oil bath and is equipped with a stirrer, Dean-Stark trap with condenser, and a nitrogen purge throughout the whole system. Degassing of the reactants and system is done by alternately evacuating with a vacuum pump and filling with nitrogen. A flow of nitrogen of about 100 ml per minute is begun and maintained throughout the reaction.

The reaction is stirred and heating is begun at a rate of about 2° C. per minute. Reaction commences at about 215° C. to 225° C. Phenol and water collect in the Dean-Stark trap. As the temperature increases and reaction proceeds, the mass becomes so stiff that stirring is impossible. The stirring should be stopped when the temperature reaches 250° C. to 255° C. and about 15 ml of condensate has been collected. After the stirrer is stopped, the mass foams and fills the flask about three quarters full. The polymer is heated to 290° C. and is held there for 1.5 hours. About 22 ml of condensate is recovered.

On cooling, the friable prepolymer is removed from the flask and is crushed.

For the second stage of polymerization, the prepolymer is charged into a flask and degassed in the same manner as in the first stage. A nitrogen sweep of 60 to 120 ml per minute is used throughout the second stage. After immersion of the reactor in a heating bath, the temperature is raised at a rate of about 1.50 per minute from 220° C. to 385° C. Polymerization is continued at 385° C. for three hours. After cooling and removal from the flask, a granulated copolymer that is about 28% by weight rigid-rod is recovered.

EXAMPLE 75

The procedure of Hart for the preparation of poly(methyl methacrylate), given in *Macromolecular Synthesis;* J. A. Moore, Ed., John Wiley & Sons; New York; 1977, Coll. Vol. 1, pp. 23–25 (incorporated herein by this reference), is followed, except that 1 g of the acrylyl-substituted macromonomer of Example 29 is added as a comonomer. A three-liter three-necked flask is charged with 1.5 liters of distilled water, 15 grams of Cyanamer A-379 (a water soluble modified polyacrylamide resin available from American Cyanamid Company as a free-flowing powder), 8.5 grams of disodium phosphate ($Na_2HPO_4$), and 0.5 gram of monosodium phosphate ($NaH_2PO_4$). The flask is fitted with a thermometer, a condenser, and a glass stirrer of the half-moon type; the mixture is warmed to 30°–35° C. and stirred until a clear solution is obtained.

In a one liter beaker are mixed 500 grams of distilled methyl methacrylate, one gram of the acrylyl-substituted macromonomer of Example 29, and 5 grams of benzoyl peroxide. When the peroxide has been completely dissolved, the solution is added to the flask. The half-moon paddle is adjusted to about one-half inch below the top surface, and agitation is begun at about 400 rpm. The reactor is flushed lightly with nitrogen gas for one to two minutes to remove atmospheric oxygen. The agitator speed is adjusted to 250 rpm, and the reaction mixture is heated to 76°–78° C. This temperature is maintained for 2.5 to 3 hours. After the mixture is cooled to room temperature, the polymer is recovered by filtration in a Buchner funnel. The polymer is washed several times with water and dried at 65° C. for 5–10 hours. The resulting copolymer is approximately 6% by weight rigid-rod.

EXAMPLE 76

In a flamed 500 ml nitrogen flask equipped with a magnetic stirrer, 8.647 g (42.59 mmol) of isophthaloyl dichloride, 10,000 g (43.81 mmol) of bisphenol-A, 5.000 g (1.22 mmol) of the chlorocarbonyl-substituted macromonomer prepared by reacting the carboxy-terminated macromonomer of Example 65 with thionyl chloride, 100 ml of 1,1,2,2-tetrachloroethane and 15 ml of pyridine are added under nitrogen pressure and heated at 120° C. for 20 hours. The copolymer is precipitated in methanol, filtered, redissolved in chloroform, reprecipitated in methanol, filtered, and dried at 80°–100° C. i.vac. The resulting copolymer is approximately 25% by weight rigid-rod.

EXAMPLE 77

The epoxy-terminated macromonomer of Example 62 (45 g) is mixed with the diglycidyl ether of bisphenol-A (EPON 825, commercially available from Shell Chemical Co.) to form Part I of a two-part epoxy. Part II is formed using triethylene tetramine (TETA) as a curing agent. The cured epoxy resin is formed by mixing TETA (12.8 g) with Part I (100 g).

EXAMPLE 78

A mixture consisting of the ester-functionalized macromonomer of Example 7 (5 g) and poly-e-caprolactam (95 g) is heated to about 240° C. and mixed until well blended. Under these conditions, the macromonomer is chemically incorporated into the polyamide via transamination. The resulting copolymer is approximately 5% by weight rigid-rod.

EXAMPLE 79

A mixture consisting of the ester-functionalized macromonomer of Example 7 (5 g) and polyethylene terephthalate (95 g) is heated to about 260° C. and mixed until well blended. Under these conditions, the macromonomer is chemically incorporated into the polyester via transesterification. The resulting copolymer is approximately 5% by weight rigid-rod.

EXAMPLE 80

A mixture consisting of the hydroxy-functionalized macromonomer of Example 38 (5 g), bisphenol-A polycarbonate (95 g), and lithium stearate (0.05 g) is heated to about 280° C. and mixed until well blended. Under these conditions, the macromonomer is chemically incorporated into the polycarbonate via transesterification. The resulting copolymer is approximately 5% by weight rigid-rod.

EXAMPLE 81

A mixture of the ester functionalized macromonomer of Example 4 (0.65 g), caprolactam (13 g) and 0.5 g of 50% aqueous aminocaproic acid as the catalyst was heated in a nitrogen purged tube for about 4–6 hours at approximately 280° C. in a sand bath and then allowed to cool. The copolymer, which is approximately 5–10% by weight rigid-rod, was obtained as a light yellow powder after crushing, extracting with boiling water for about 8 hours, and vacuum drying at 50° C.

The above descriptions of exemplary embodiments of macromonomers having functional end groups, the rigid-rod polymers, copolymers, and resins prepared therefrom, and the processes for making same are illustrative of the present invention. Because of the variations which will be apparent to those skilled in the art, however, the present invention is not intended to be limited to the particular embodiments described above. The scope of the invention is defined in the following claims.

What is claimed is:

1. A rigid-rod macromonomer of the formula:

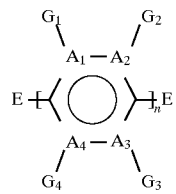

wherein each $A_1$, $A_2$, $A_3$, and $A_4$, on each monomer unit, independently, is C or N; each $G_1$, $G_2$, $G_3$, and $G_4$, on each monomer unit, independently, is H or a solubilizing side group, provided that at least one monomer unit has at least one solubilizing side group, wherein said solubilizing side groups provide macromonomers with a solubility of at least 0.5% by weight in the solvent system from which they are formed, and provided that when any of $A_1$, $A_2$, $A_3$, and $A_4$ is N, the corresponding $G_1$, $G_2$, $G_3$, or $G_4$ is nil, wherein said solubilizing side groups G are selected from the group consisting of Phenyl, biphenyl, naphthyl, phenanthryl, anthracenyl, benzyl, benzoyl, naphthoyl, phenoxy, phenoxyphenyl, phenoxybenzoyl, alkyl, alkyl ketone, aryl, aryl ketone, aralkyl, alkaryl, alkoxy, aryloxy alkyl ester, aryl ester, amide, alkyl amide, dialkyl amide, aryl amide, diaryl amide, alkyl aryl amide, amides of cyclic amines such as piperidine, piperazine and morpholine, alkyl ether, aryl ether, alkyl sulfides, aryl sulfides, alkyl sulfones, aryl sulfones, thioether, fluoro, trifluoromethyl, perfluoroalkyl, and pyridyl, where alkyl is a linear or branched hydrocarbon chain having between 1 and 30 carbon atoms, and aryl is any single, multiple or fused ring aromatic or heteroaromatic group having between 3 and 30 carbon atoms, and fluorine-substituted analogs of the aforementioned G groups; E is a reactive end group selected from the group consisting of acetals, acetylenes, acetyls, acid anhydrides, acrylamides, acrylates, aldehydes, alkyl aldehydes, amides, amines, anilines, aryl aldehydes, azides, benzocyclobutenes, biphenylenes, carboxylates, carboxylic anhydrides, cyanates, cyanides, epoxides, esters, ethers, formyls, fulvenes, heteroaryls, hydrazines, hydroxylamines, imides, imines, isocyanates, ketals, ketoalkyls, ketoaryls, ketones, maleimides, nadimides, nitriles, olefins, phenols, phosphates, phosphonates, silanes, silicates, silicones, silyl ethers, styrenes, sulfonamides, sulfones, sulfonic acids and their salts, sulfoxides, tetrahydropyranyl ethers, thioethers, urethanes, vinyl ethers, and vinyls; the macromonomer has an average degree of polymerization, $DP_n$, greater than 6; and adjacent monomer units are oriented head-to-head, head-to-tail, or randomly.

2. A macromonomer according to claim 1, wherein the solubilizing side group is selected from the group consisting of alkyls, amides, aryls, aryl sulfides, aryl sulfones, esters, ethers, thioethers, fluoroalkyls, and ketones.

3. A macromonomer according to claim 1, wherein $G_1$ is an arylketone and E is an amine-derived end group.

4. A macromonomer according to claim 1, wherein $G_1$ is an arylketone and E is selected from the group consisting of amides, carboxylic acids, carboxylic acid halides, carboxylic anhydrides, and esters.

5. A macromonomer according to claim 1, wherein $G_1$ is an arylketone and E comprises an alcohol.

6. A macromonomer according to claim 1, wherein $G_1$ is an arylketone and E is selected from the group consisting of epoxide, vinyl, and imide groups.

7. A macromonomer according to claim 1, wherein $G_1$ is an aryl group and E is an amine-derived end group.

8. A macromonomer according to claim 1, wherein $G_1$ is an aryl group and E is selected from the group consisting of amides, carboxylic acids, carboxylic acid halides, carboxylic anhydrides, and esters.

9. A macromonomer according to claim 1, wherein $G_1$ is an aryl group and E comprises an alcohol.

10. A macromonomer according to claim 1, wherein $G_1$ is an aryl group and E is selected from the group consisting of epoxide, vinyl, and imide groups.

11. A macromonomer according to claim 1, wherein $G_1$ is an aryl ether and E is an amine-derived end group.

12. A macromonomer according to claim 1, wherein $G_1$ is an aryl ether and E is selected from the group consisting of amides, carboxylic acids, carboxylic acid halides, carboxylic anhydrides, and esters.

13. A macromonomer according to claim 1, wherein $G_1$ is an aryl ether and E comprises an alcohol.

14. A macromonomer according to claim 1, wherein $G_1$ is an aryl ether and E is selected from the group consisting of epoxide, vinyl, and imide groups.

15. A macromonomer according to claim 1, wherein $G_1$ is an amide and E is an amine-derived end group.

16. A macromonomer according to claim 1, wherein $G_1$ is an amide and E is selected from the group consisting of amides, carboxylic acids, carboxylic acid halides, carboxylic anhydrides, and esters.

17. A macromonomer according to claim 1, wherein $G_1$ is an amide and E comprises an alcohol.

18. A macromonomer according to claim 1, wherein $G_1$ is an amide and E is selected from the group consisting of epoxide, vinyl, and imide groups.

19. A rigid-rod macromonomer of the formula:

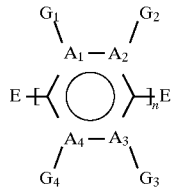

wherein each $A_1$, $A_2$, $A_3$, and $A_4$, on each monomer unit, independently, is C or N; each $G_1$, $G_2$, $G_3$, and $G_4$, on each monomer unit, independently, is selected from the group consisting of H, solubilizing side groups, and reactive side groups, provided that at least one monomer unit has at least one solubilizing side group, wherein said solubilizing side groups provide macromonomers with a solubility of at least 0.5% by weight in the solvent system from which they are formed, and provided that when any of $A_1$, $A_2$, $A_3$, and $A_4$ is N, the corresponding $G_1$, $G_2$, $G_3$, or $G_4$ is nil, wherein said solubilizing side groups G are selected from the group consisting of phenyl, biphenyl, naphthyl, phenanthryl, anthracenyl, benzyl, benzoyl, phenoxybenzoyl, alkyl, alkyl ketone, aryl, aryl ketone, aralkyl, alkaryl, alkoxy, aryloxy, alkyl ester, aryl ester, amide, alkyl amide dialkyl amide, aryl amide, diaryl amide, alkyl aryl amide, amides of cyclic amines such as piperidine piperazine and morpholine, alkyl ether, aryl ether, alkyl sulfides, aryl sulfides, alkyl sulfones, aryl sulfones, thioether, fluoro, trifluoromethyl, perfluoroalkyl, and pyridyl, where alkyl is a linear or branched hydrocarbon chain having between 1 and 30 carbon atoms, and aryl is any single, multiple or fused ring aromatic or heteroaromatic group having between 3 and 30 carbon atoms, and fluorine-substituted analogs of the aforementioned G groups; E is a reactive end group; the macromonomer has a degree of polymerization, $DP_n$, greater than about 6: and adjacent monomer units are oriented head-to-head, head-to-tail, or randomly; wherein the reactive side groups and reactive end groups E are independently selected from the group consisting of acetals, acetylenes, acetyls, acid anhydrides, acrylamides, acrylates, aldehydes, alkyl aldehydes, alkyl halides, amides, amines, anilines, aryl aldehydes, azides, benzocyclobutenes, biphenylenes, carboxylates, carboxylic anhydrides, cyanates, cyanides, epoxides, esters, ethers, formyls, fulvenes, heteroaryls, hydrazines, hydroxylamines, imides, imines, isocyanates, ketals, ketoalkyls, ketoaryls, ketones, maleimides, nadimides, nitrites, olefins, phenols, phosphates, phosphonates, silanes, silicates, silicones, silyl ethers, styrenes, sulfonamides, sulfones, sulfonic acids and their salts, sulfoxides, tetrahydropyranyl ethers, thioethers, urethanes, vinyl ethers, and vinyls.

20. A rigid-rod macromonomer according to claim 19, wherein at least one monomer unit has at least one reactive side group.

21. A rigid-rod macromonomer according to claim 19, wherein a plurality of monomer units have at least one reactive side group.

22. A rigid-rod macromonomer of the formula:

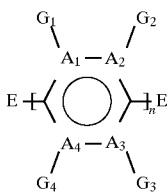

wherein each $A_1$, $A_2$, $A_3$, and $A_4$, on each monomer unit, independently, is C or N; each $G_1$, $G_2$, $G_3$, and $G_4$, on each monomer unit, independently, is H or a solubilizing side group, provided that at least one monomer unit has at least one solubilizing side group wherein said solubilizing side groups provide macromonomers with solubility of at least 0.5% by weight in the solvent system from which they were formed, and provided that when any of $A_1$, $A_2$, $A_3$, and $A_4$ is N, the corresponding $G_1$, $G_2$, $G_3$, or $G_4$ is nil; E is a reactive end group; the macromonomer has an average degree of polymerization, $DP_n$, greater than 6; and adjacent monomer units are oriented head-to-head, head-to-tail, or randomly; the combinations of $G_1$ and E selected from the group consisting of the following:

1) $G_1$ is an arylketone and E is an amine-derived end group;
2) $G_1$ is an arylketone and E is selected from the group consisting of amides, carboxylic acids, carboxylic acid halides, carboxylic anhydrides, and esters;
3) $G_1$ is an arylketone and E comprises an alcohol;
4) $G_1$ is an arylketone and E is selected from the group consisting of epoxide, vinyl, and imide groups;
5) $G_1$ is an aryl group and E is an amine-derived end group;
6) $G_1$ is an aryl group and E is selected from the group consisting of amides, carboxylic acids, carboxylic acid halides, carboxylic anhydrides, and esters;
7) $G_1$ is an aryl group and E comprises an alcohol;
8) $G_1$ is an aryl group and E is selected from the group consisting of epoxide, vinyl, and imide groups;
9) $G_1$ is an aryl ether and E is an amine-derived end group;
10) $G_1$ is an aryl ether and E is selected from the group consisting of amides, carboxylic acids, carboxylic acid halides, carboxylic anhydrides, and esters;
11) $G_1$ is an aryl ether and E comprises an alcohol;
12) $G_1$ is an aryl ether and E is selected from the group consisting of epoxide, vinyl, and imide groups;
13) $G_1$ is an amide and E is an amine-derived end group;
14) $G_1$ is an amide and E is selected from the group consisting of amides, carboxylic acids, carboxylic acid halides, carboxylic anhydrides, and esters;
15) $G_1$ is an amide and E comprises an alcohol; and
16) $G_1$ is an amide and E is selected from the group consisting of epoxide, vinyl, and imide groups.

23. A rigid-rod macromonomer of the formula:

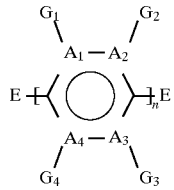

wherein each $A_1$, $A_2$, $A_3$, and $A_4$, on each monomer unit, independently, is C or N; each $G_1$, $G_2$, $G_3$, and $G_4$, on each monomer unit, independently, is H or a solubilizing side group, provided that at least one monomer unit has at least one solubilizing side group, wherein said solubilizing side groups provide macromonomers with solubility of at least 0.5% by weight in the solvent system from which they were formed, and provided that when any of $A_1$, $A_2$, $A_3$, and $A_4$ is N, the corresponding $G_1$, $G_2$, $G_3$, or $G_4$ is nil, wherein said solubilizing side groups G are selected from the group consisting of phenyl, biphenyl, naphthyl, phenanthryl, anthracenyl, benzyl, benzoyl, naphthoyl, phenoxy, phenoxyphenyl, phenoxybenzoyl, alkyl, alkyl ketone, aryl, aryl ketone, aralkyl, alkaryl, alkoxy, aryloxy, alkyl ester, aryl ester, amide, alkyl amide, dialkyl amide, aryl amide, diaryl amide, alkyl aryl amide, amides of cyclic amines such as piperidine, piperazine and morpholine, alkyl ether, aryl ether, alkyl sulfides, aryl sulfides, alkyl sulfones, aryl sulfones, thioether, fluoro, trifluoromethyl, perfluoroalkyl, and pyridyl, where alkyl is a linear or branched hydrocarbon chain having between 1 and 30 carbon atoms, and aryl is any single, multiple or fused ring aromatic or heteroaromatic group having between 3 and 30 carbon atoms, and fluorine-substituted analogs of the aforementioned G groups; E is a reactive end group selected from the group consisting of acetals, acetals from ethylvinylether, acetylenes, acetyls, acid anhydrides, acids, acrylamides, acrylates, alcohols, aldehydes, alkyl aldehydes, alkyl halides, amides, amines, anilines, aryl aldehydes, azides, benzocyclobutenes, biphenylenes, carboxylates, carboxylic acids and their salts, carboxylic acid halides, carboxylic anhydrides, cyanates, cyanides, epoxides, esters, ethers, formyls, fulvenes, halides, heteroaryls, hydrazines, hydroxylamines, imides, imines, isocyanates, ketals, ketoalkyls, ketoaryls, ketones, maleimides, nadimides, nitriles, olefins, phenols, phosphates, phosphonates, quaternary amines, silanes, silicates, silicones, silyl ethers, styrenes, sulfonamides, sulfones, sulfonic acids and their salts, sulfonyl halides, sulfoxides, tetrahydropyranyl ethers, thioethers, urethanes, vinyl ethers, and vinyls; the macromonomer has a degree of polymerization, $DP_n$, greater than 15; and adjacent monomer units are oriented head-to-head, head-to-tail, or randomly.

24. A macromonomer according to claim 23, wherein the solubilizing side group is selected from the group consisting of alkyls, amides, aryls, aryl sulfides, aryl sulfones, esters, ethers, thioethers, fluoroalkyls, and ketones.

25. A soluble rigid-rod macromonomer of the formula:

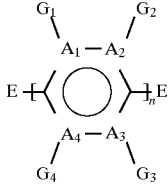

wherein each $A_1$, $A_2$, $A_3$, and $A_4$, on each monomer unit, independently, is C or N; each $G_1$, $G_2$, $G_3$, and $G_4$, on each monomer unit, independently, is H or a solubilizing side group, provided that at least one monomer unit has at least one solubilizing side group, wherein said solubilizing side groups provide macromonomers with solubility of at least 0.5% by weight in the solvent system from which they were formed, and provided that when any of $A_1$, $A_2$, $A_3$, and $A_4$ is N, the corresponding $G_1$, $G_2$, $G_3$, or $G_4$ is nil, wherein said solubilizing side groups G are selected from the group consisting of phenyl, biphenyl, naphthyl, phenanthryl, anthracenyl, benzyl, benzoyl, naphthoyl, phenoxy, phenoxyphenyl, phenoxybenzoyl, alkyl, alkyl ketone, aryl, aryl ketone, aralkyl, alkaryl, alkoxy, aryloxy, alkyl ester, aryl ester, amide, alkyl amide, dialkyl amide, aryl amide, diaryl amide, alkyl aryl amide, amides of cyclic amines such as piperidine, piperazine and morpholine, alkyl ether, aryl ether, alkyl sulfides, aryl sulfides, alkyl sulfones, aryl sulfones, thioether, fluoro, trifluoromethyl, perfluoroalkyl, and pyridyl, where alkyl is a linear or branched hydrocarbon chain having between 1 and 30 carbon atoms, and aryl is any single, multiple or fused ring aromatic or heteroaromatic group having between 3 and 30 carbon atoms, and fluorine-substituted analogs of the aforementioned G groups; E is a reactive end group selected from the group consisting of alkyl halides, sulfonyl halides, and carboxylic acid halides; the macromonomer has an average degree of polymerization, $DP_n$, greater than 6; and adjacent monomer units are oriented head-to-head, head-to-tail, or randomly.

26. A macromonomer according to claim 25, wherein the solubilizing side group is selected from the group consisting of alkyls, amides, aryls, aryl sulfides, aryl sulfones, esters, ethers, thioethers, fluoroalkyls, aryl ketones and alkyl ketones.

27. A macromonomer according to claim 26, wherein $G_1$ is an aryl ketone.

28. A macromonomer according to claim 26, wherein $G_1$ is benzoyl.

29. A macromonomer according to claim 25, wherein the reactive end group E is a carboxylic acid halide.

30. A macromonomer according to claim 25, wherein the reactive end group E is an alkyl halide.

31. A macromonomer according to claim 25, wherein the reactive end group E is a sulfonyl halide.

* * * * *

UNITED STATES PATENT AND TRADEMARK OFFICE
CERTIFICATE OF CORRECTION

PATENT NO. : 5,827,927
DATED : October 27, 1998
INVENTOR(S) : Robert R. Gagné; Matthew Louis Marrocco III; Mark Steven Trimmer; Neil H. Hendricks It is certified that error appears in the above-identified patent and that said Letters Patent is hereby corrected as shown below:

Column 7,
Lines 55,56, take out the spaces between "that the" and "properties".

Column 10,
Line 5, the copolymer should read:

Column 11,
Line 21, change "nrovolac" to -- novolac --.
Line 31, change "in,," to -- in, --.

Column 12,
Line 14, change "proformed" to -- preformed --.

Column 14,
Line 1, change "Flourine-" to -- Fluorine- --.
Line 42, change "G2" to -- $G_2$ --.

Column 23,
Line 59, change "$2_L$" to -- 2L --.

Column 24,
Line 54, change "deepred" to -- deep-red --.

Column 26,
Line 15, change "mmoi" to -- mmol --.

Column 27,
Line 67, change "4-chloroace-tophenone" to -- 4-chloroacetophenone --.

Column 28,
Line 54, change "$Dp_n$20-25" to -- $Dp_n \approx$20-25 --.

Column 29,
Line 26, change "mmiol" to -- mmol --.
Lines 52,53, the structure should read:

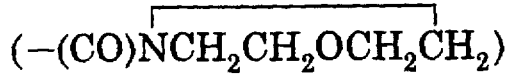

UNITED STATES PATENT AND TRADEMARK OFFICE
CERTIFICATE OF CORRECTION

PATENT NO. : 5,827,927
DATED : October 27, 1998
INVENTOR(S) : Robert R. Gagńe; Matthew Louis Marrocco III; Mark Steven Trimmer; Neil H. Hendricks It is certified that error appears in the above-identified patent and that said Letters Patent is hereby corrected as shown below:

Column 31,
Line 47, "4-chloro-2-meth-oxy-5-" should read -- 4-chloro-2-methoxy-5 --.

Column 32,
Line 49, change "structure 1" to -- structure (1) --.
Line 60, change "structure 1" to -- structure (1) --.

Column 33,
Line 57, change "structure 1" to -- structure (1) --.

Column 34,
Line 19, after "$G_1$" delete the comma.
Line 38, change "2-chloro-4'-(N-succini-mido)" to -- 2-chloro-4'-(N-succinimido) --.
Line 56, change "cis-5-norbor-nene-" to -- "cis-5-norbornene --.

Column 35,
Line 3, change "2-chloro-4'-(N-succini-mido)" to -- 2-chloro-4'-(N-succinimido) --.
Line 32, change "obromide" to -- bromide --.
Line 42, change "$G_2$form" to -- $G_2$ form --.

Column 36,
Line 39, change "2-bipheny-lene" to -- 2-biphenylene --.
Line 54, change "2-bipheny-lene" to -- 2-biphenylene --.
Line 59, change "structure 1" to -- structure (1) --.

Column 39,
Line 50, replace "EXAMPLES 68-82" with -- EXAMPLES 68-81 --.

Column 40,
Line 61, replace "Examiner" with -- Example --.
Line 65, change "half way" to -- halfway --.

Column 41,
Line 20, after "tapping with" insert -- a --.
Line 28, change "[2,2'-(p,p'-oxydipheny-lene)-6" to -- [2,2'-(p,p'-oxydiphenylene)-6 --.

UNITED STATES PATENT AND TRADEMARK OFFICE
CERTIFICATE OF CORRECTION

PATENT NO. : 5,827,927
DATED : October 27, 1998
INVENTOR(S) : Robert R. Gagńe; Matthew Louis Marrocco III; Mark Steven Trimmer; Neil H. Hendricks It is certified that error appears in the above-identified patent and that said Letters Patent is hereby corrected as shown below:

<u>Column 43,</u>
Line 4, change "1.50" to -- 1.5° --.

<u>Column 44,</u>
Line 67, change "Phenyl" to -- phenyl --.

Signed and Sealed this

Eighth Day of January, 2002

Attest:

*Attesting Officer*

JAMES E. ROGAN
*Director of the United States Patent and Trademark Office*